(12) United States Patent
Vasta et al.

(10) Patent No.: US 6,326,485 B1
(45) Date of Patent: Dec. 4, 2001

(54) ASSAY FOR PERKINSUS IN SHELLFISH

(75) Inventors: Gerardo Vasta, Columbia, MD (US); Adam G. Marsh, Los Angeles, CA (US); Joséto A. Fernández-Robledo, Baltimore, MD (US); Cathleen A. Coss, Hagerstown, MD (US); Anita C. Wright, Woodstock, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 08/900,117

(22) Filed: Jul. 25, 1997

Related U.S. Application Data

(60) Provisional application No. 60/023,345, filed on Jul. 26, 1996.

(51) Int. Cl.$^7$ .................................................. C07H 21/04
(52) U.S. Cl. ...................... 536/24.3; 536/24.31; 439/91.2
(58) Field of Search ..................... 435/6, 91.2; 536/24.3, 536/24.31, 24.33

(56) References Cited

U.S. PATENT DOCUMENTS 5,585,238 * 12/1996 Ligon et al. .............................. 435/6

OTHER PUBLICATIONS

Henriques et al., Yease 7:167–172, 1991.*

Adam G. Marsh et al., A Semiquantitative PCR Assay for Assessing Perkinsus Marinus Infections in the Eastern Oyster, Crassostrea Virginica, J. Parasitol . . . 81(4), Aug., 1995, pp. 577–583.

* cited by examiner

*Primary Examiner*—Scott W. Houtteman
(74) *Attorney, Agent, or Firm*—Blank Rome Comisky & McCauley, LLP

(57) ABSTRACT

The present invention is directed to oligonucleotides used as amplification primers and assay probes for species-specific detection and identification of the protozoan Perkinsus in shellfish. The oligonucleotides are designed to preferentially hybridize to what has been found to be a species-unique sequence in the target organism's genome. Preferential hybridization means, for example, that the inventive primers amplify the target sequence in *P. marinus* with little or no detectable amplification of target sequences of other species of protozoa such as *P. atlanticus* thereby making the assay species specific.

17 Claims, 17 Drawing Sheets rRNA Gene Cluster

```
  1                                                                               50
  AAAGTCGCAC CTTTCCCCAT AAACCCCCTC CCCACCCCCT TGGACATTGT
 51                                                                              100
  TCCACTTTTC ACTTGTATTG TGAAGCACCC AATGCTAGCC CATAGAACAG
101                                                                              150
  TCCAGTAGTT CAATAGAGAG ACTAGTGAAC ATAGTTTATA ACATTGTCCA
151                                                                              200
  AGGGGTGGAG GGGGATGCGC GAAATCGATG TGCACGTTTG GTCAAAGATG
201                                                                              250
  CTCGCGAAAG CTGCACATCA ATTTCGCACA TGGGCGAAAT TGACTTGCAG
251                                                                              300
  GTGGGTATAA AAGTTGATGT AGGCCATGTG GCTCGATTTC AACCATATGG
301                                                                              350
  GTATGCTTCT GAGGATGGGG TGTTACAGTG GACCATATGA GGTAGGTCAT
351                                                                              400
  TTGGAGATGT CACCAAAATG GTCTAAATCT GCGCATTCCA TTTAAGTGAA
401                                                                              450
  TTTAAGTGAA ATTTAAGTGA ATTTTACTTA AAATTGACCT TTTTCGTTGC
451                                                                              500
  GCAGATTTGG GGTGGTGATG GGTGACGCGG CGAATTTTTT AAAAAAGAGG
500                                                                              550
  TATATCGCGT GCTATTTGTA TTTTTGGTAT CACCGCGTCA CCAATCACCA
551                                                                              600
  TTGACGGTTT CTTTTTCGAA GTTTTTCCGG ATTATTGCAT TTTTTATATA
600                                                                              650
  ATTGTGGGTG GCTGATTCTT GCGAAGGAC  TGTTGTGATG TCCGAGTTCC
651                                                                              700
  CAAATTGGGA GTTTTTGGAC ATCACTCCTG ATCTGCCGGC GGCGATCAGG
700                                                                              750
  ATGACTGACA TTTCGATATA TTTTGGGTAT TCGATAGCTG CCAAATCGGT
751                                                                              800
  CAGCGTCGAG TATTCCGGTT TATTCGAAGG ATTCATGATA TTGCAAAATA
800                                                                              850
  TCATTGATTT TCATGGGGTT TTGTATTAGT ACCCGCTCAT TGTGGGAAAG
851                                                                              900
  TCGGGTGGAT TTATCTTACC CGCAAATCTA ATACAAGATT TGCATGATGC
900                                                                              950
  AGCAATAGAC CAAGGTTAGT ATAGCAGTTG TATTTATACG ACTAGTTATG
951                                                                             1000
  CAAACCCTTT GTGTTTTTTG TTGCGACTCT TGGCGTGAAC CGGAAGACCG
1000                                                                            1050
  GACCTCGCTT TCGACTATTC ATCTTTGATG GATATGAGAT CGCAAGGGTA
1051                                                                            1100
  TCGCTTCGTG CGATATTTAG TGACCATCAG AGCACGCTAC GACTTTTGAT
1100                                                                            1150
  TATATCCTTG GATTTAATCG GAAGCTCGCA AGCATTGCAT TGATGCAATC
```

FIG. 2

```
1                                                 50
TTTTTGCTTT CACAACCCCG CACCCCATGT ACAATGTTGC CAACCACTAG
51                                                100
AGTTTCAACA ACATTCGGAT TTGACAACAT GTCAACAATT CACAACAGAA
101                                               150
ATTGACAACA TTGTCACAAA TTCTCAAATT GGACAACATT GGACAAAAAT
151                                               200
TCACAACATA CATTGGACAA CAGTGGACAA CGAACCCAAA CCCGACAACA
201                                               250
TTGTCCAGGG GGATAGGGGG TGAAAAAGCA GTGCCGGCAA AGTCGAAAGA
251                                               300
TGTCAAGTTG GAATGCGGCT CAAATTCGTC ATTTGTGTAA ATCCGCAATT
301                                               350
TTGCCAATGT GCAATTTTGC AAATGTGCAA TTTTGCAAAT GTGCAATTTT
351                                               400
GCCAATGTGC AATTTTGCAA ATGCGCAATT TTGCAAATCC GCAATTTTGC
401                                               450
AAATGTGCAA TTTTGGAAAA TCACCAAATG AAAATCGTCC AAGTCGAATT
451                                               500
GGAGGCGTGG TGACATGGTC CCGGGATCCC CTGGTTACAG TGGACAATAT
500                                               550
CCCAGCAATA TTCGCTGTAA TTTGGAGTTT CGCTGTTTTG GCAAATTTTG
551                                               600
AGTCTGAAAA AAAAAATTGC AAATGCGCAA AGGGGGTGAA GGAAAAAAAA
600                                               650
GCACCCCCGA AGGTAAAATT CCCTTTAAGT CCCTTGCGCA TTTGCAAAAT
651                                               700
TTTCAAAAAT TGTTGCAAAT GCGCTTTTGT TATTTGGCCG GTTCATTGGT
700                                               750
GTCAAAAGTT GCCTGGGGTG GTTACACAAT GCACGGAATT GGTTGGAAGT
751                                               800
TGTGTGATTG AAAATTGGTC GTGTCACACA ATTTTGCGCA TTTGCAAAAA
800                                               850
TTCGCAAATT GGACAAAAAA GGGTCGCGCA CAGTCAAATT GCGCAAATTT
851                                               900
CACTTTGAAG TGAGTGCGCA TTTGTGGGGC AGAAATGTGG TGACAGCATC
900                                               950
GTTTTTTATA ATAAATATTC TATATTTAGT ATCTTTATTA TAATTTGCTG
951                                               1000
TCACCAATCA CCATTTTAGA ATTTTTATTT TTTTATGTTT TAGTGACCGC
1000                                              1050
GGGATTTTTT GCAAAGTACT ATYGTGATGT TTGAGTTGTT TGAAATGGGC
1051                                              1100
AATTTAGAAC ATCATCAGAA ATCGCTGAAT AGTGATTTTT GAGTTTGACT
1100                                              1150
GTTTGAAGTG TTTTGGGTAT TCGGCAGCTG CCAAATCGGT CAGCGTCGAA
1151                                              1200
TATAATAGCA TTTTTGTGTG TATATGATAT TTAGCGATAT CATTGGAATC
```

FIG. 3A

```
1200                                              1250
ATGGGGTTTT GTATTAGTAC CCGCTCATTG TGGGAATGTC GGGTGGTTCA
1251                                              1300
ATATCACCTG CAAATTTAAT ACAGGATTTG CATGATGCAG CGACTGACCG
1300                                              1350
GGGTTGGTAT AATAGCTGAT TATTCGGCTT ATTATGCAGA CCTATCGTGT
1351                                              1400
TAGTAGTTGC GACTCTTGGC GTGAACCGGA AGACCGGAAC TTGAATTCGA
1400                                              1450
CTATTTACGT CCGTAAACAG GAGATTTCAA GAATATTGCA CATTTTGCGT
1451                                              1500
GATATAAACG TGATCATCTG AGCACGCTTC GACTCTTGGA TATCTGCTAA
1500                                              1550
TCAGCCGTCA TCTGAGAGCT CGCAAGCATT GCAATTGATG CAATC
```

FIG. 3B

```
1                                                              50
CGTGCCCTTT TCACGAATTC ACAGCCCCGC ACCCCATGTA CAATGTTGCC
51                                                             100
CACCCGAAAT GCCTGCCTGC CCACCCGAAA TGCCCGAAAT GCCCGTTAGA
101                                                            150
AAAAGTATGC GAAAAGTTCT TGTCAATTTT GACAGTGTGT GAAAAAACTG
151                                                            200
AAAAAGTCCA CTCAACATTG CATTATGCAA TTTGCCACTC AACATTGTCC
201                                                            250
AGGGGGATAG GGGGTGAAAA AGTATCGCAG TCCAACTGAA AAGATGCTAA
251                                                            300
GTTGAAATGC GGCGCAAATT CATCACTTGA GTTGCGAAAA TCCCTAAAGT
301                                                            350
CGAATTTGGC ACTCGGTGAC ATGATCGGGA ATTTCCTGG TTACAGTGGT
351                                                            400
CAAATCCCAG CAATTTTGGC AAAGTTTTTG AGTTTCGCAC TTTTCGCAAA
401                                                            450
TTTCGTGTCT GAAAAAAAAA TTTCAACTTT GCGCAAAGGG GTCAAAGGGA
451                                                            500
AAAAAAGCAC CCTCAAAAGG AAATTTCCCT TTAATCCCCT TTGAAAAAAA
500                                                            550
TGCGCAAAGT TAAATTTGCG AAAATTTCGA TTTTCTCATA TGACCGATTA
551                                                            600
GTTGGTGCCA GATGGTAGTC GGGATGGTTA CACGGTGCAC GGAACTCGTT
600                                                            650
GGAAGTTCTG GAGTTACGAA TTGGTCCCGT CACCACAATT TGCGCATTTT
651                                                            700
TGAAATTGCG CAAATTTGCG AAAAAAGCAG CGCGCAAAGT TAAATTGTGC
700                                                            750
GAAAATTGAC TTTCAGGTCG GTGCGCAAAT TTGGGGTGAA AAAGTGGTGA
751                                                            800
CAGCATCAGA ATTATAATAA ATAATCTATA ATCTAGTTCT TTTATTATAA
800                                                            850
TTAGCTGTCA CCAATCACCA TTTGAGATTT TTTATTTTTT TATGTTTTAG
851                                                            900
TGACCGCGGT ATTTTTTCCA GAGTACTATC GTGATGTCTG AGTTGTCTAA
900                                                            950
AACGGCAATT TCAGAACATT ACCAGAAAAC ACTGAATAGT GGTTTCTGAG
951                                                            1000
TCTGACTGTT TGAAGTGTTT TGGGTATTCG GCAGCTGCCA ATTCGGCAG
1000                                                           1050
GGTTGAATAT ACTAACATTT CTGTGTGTAT ATGGTATTTA GCGATATCAT
1051                                                           1100
```

FIG. 4A

```
TGGAATCATG GGGTTTTGTA TTAGTACCCG CTCATTGTGG GAAAGTCGGG
1100                                                 1150
TGGTTCAATA TCACCTGCAA ATTTAATACA GGATTTGCAT GATGCAGCGA
1151                                                 1200
CTGACCGGGG TTAGTATAAT AGCTGATTAT TCGGCTTATT ATGCAGACCT
1200                                                 1250
ATCGTGTTAG TAGTTGCGAC TCTTGGCGTG AACCGGAAGA CCGGAACTTG
1251                                                 1300
ATTTCGACTA TTTACGTCCG TAACACGTCC GTAAACAGGA GATTTCAAGA
1300                                                 1350
ATATTGCACA TTTTGTGTGA TATAATCGTG ATCATCTGAG CACGCTTCGA
1351                                                 1400
CTCTTGAATA TTTGTTAAAC AACCGATATT CGGGAGCTCG CAAGCATTGC
1400                                                 1450
AATTGATGCA ATC
```

FIG. 4B

| Primer | Sequence | Target |
|---|---|---|
| 300 F | 5'-CACTTGTATTGTGAAGCACCC-3' | Perkinsus marinus |
| 300 R | 5'-TTGGTGACATCTCCAAATGAC-3' | |
| 500 F | 5'-ATGCTAGCCCATAGAACAGT-3' | |
| 500 R | 5'-ATGCTAGCCCACATCACAGC-3' | |
| A8-1 F | 5'-AAGTCGAATTGGAGGCGTGGTGAC-3' | Perkinsus species #2 |
| A8-1 R | 5'-ATTGTGTAACCACCCCAGGC-3' | Perkinsus species #2 |
| PM5 | 5'-ATGCTAGCCC ATAGAACAGT-3' | P. marinus type I |
| PM7 | 5'-AGGTAGGTCA TTTGGAGATG-3' | P. marinus type I |
| PM6 | 5'-ATGCTAGCCC ACATCACAGC-3' | P. marinus type II |
| PM8 | 5'-TGGTAGGTCA TTTGGAGATG-3' | P. marinus type II |

```
         1                                                        50
Type-I   CACTTGTATT GTGAAGCACC CAATGCTAGC CCATAGAACA GTCCAGTAGT
Type-II  CACTTGTATT GTGAAGCACC CAATGCTAGC CCACATCACA GCCCAGTAGT 51                                                       100
Type-I   TCAATAGAGA GACTAGTGAA CATAGTTTAT AACATTGTCC AAGGGGTGGA
Type-II  TCAATAGAGA GACGAGTGAA CATAGTTTAT AACATTGTCC AAGGGGTGGA 101                                                      150
Type-I   GGGGGATGCG CGAAATCGAT GTGCACGTTT GGTCAAAGAT GCTCGCGAAA
Type-II  GGGGGATGCG CGAAATCGAT GTGCACGTTT GGTCAAAGAT GCTCGCGAAA 151                                                      200
Type-I   GCTGCACATC AATTTCGCAC ATGGGCGAAA TTGACTTGCA GGTGGGTATA
Type-II  GCTGCACATC AATTTCGCAC ATGGGCGAAA TTGACTTGCA GGTGGGTATA 201                                                      250
Type-I   AAAGTTGATG TAGGCCATGT GGCTCGATTT CAACCATATG GGTATGCTTC
Type-II  AAAGTTGATG TAGGCCATGT GGCTCGATTT CAACCATATG GGTATGCTTC 251                                                      300
Type-I   TGAGGATGGG GTGTTACAGT GGACCATATG AGGTAGGTCA TTTGGAGATG
Type-II  TGAGGATGGG GTGTTACAGT GGACCATATG TGGTAGGTCA TTTGGAGATG 301
Type-I   TCACCAA
Type-II  TCACCAA
```

ASSAY FOR PERKINSUS IN SHELLFISH

CROSS-REFERENCE TO RELATED APPLICATION

This is a continuation-in-part of U.S. Provisional Application No. 60/023,345 filed on Jul. 26, 1996, the contents of which are incorporated herein.

FEDERAL SPONSORSHIP OF INVENTION

The U.S. Government has a paid-up license in this invention as provided for by the terms of agreement number NA47FL-0163 NOAA/NMFS awarded under the Oyster Disease Research Program by the National Oceanographic and Atmospheric Administration of the U.S. Department of Commerce.

FIELD OF THE INVENTION

The present invention relates to diagnostic assays and more particularly to diagnostic assays which utilize the polymerase chain reaction (PCR) to detect the presence and concentration of a pathogen suspected of infecting shellfish.

BACKGROUND OF THE INVENTION

A. Diseases in Shellfish (oysters, clams, and other bivalves)

Shellfish, particularly oysters, are universally recognized as important sources of commercially valuable food and as organisms that play important roles in the aquatic ecosystem as part of the food chain and in reducing the turbidity of water through filtration. Unfortunately, protozoan, bacterial, fungal and viral epizootic diseases are destroying massive numbers of natural and cultivated stocks of oysters and other shellfish in coastal areas of the United States. A clear example of the serious impact of shellfish diseases is the enormous decline in oyster production from the Chesapeake Bay. Oyster production has plummeted from a high of 2.5 million bushels harvested annually in the early 1980's to less than 1% of this level in the past few years.

Protozoan infections is a primary cause of mass mortality of the eastern oyster *Crassostrea virginica* along the Gulf of Mexico and Atlantic coasts. The major disease is "Dermo," caused by the endoparasitic protozoan *Perkinsus marinus*. This disease, for which there is no known remedy, has resulted in a critical reduction of existing populations and is a major cause of the collapse of the oyster industry in the Chesapeake Bay. The range of this parasite has now extended into low salinity areas of Chesapeake Bay tributaries that are sources of oyster seed stock. Additionally, the parasite has been detected in North Atlantic waters from Delaware Bay to Maine that were previously disease free and thought to be uninfected due to cold water conditions.

Other Perkinsus species have been detected in mollusks around the world and cause mass mortalities in commercially important shellfish from Australia and Europe. In addition to *P. marinus*, other pathogenic species include *P. olseni* in the abalone in Australia and *P. atlanticus* in the European clam.

The transplantation of brood and seed stocks between countries has become a frequently used alternative to raising native shellfish. However, this practice can also lead to the spread of disease and the destruction of native stocks because of the lack of appropriate diagnostic tests. Frequently, natural resource managers seek to introduce non-indigenous oysters having desirable characteristics to their aquatic jurisdiction. However, if the introduced species carries Dermo or other infectious diseases the consequences can be devastating.

B. Currently Available Shellfish Dermo Disease Detection Methods

The continuing decline of oyster stocks as a result of Dermo and other diseases has created a demand for new technologies to efficiently detect and monitor these diseases in indigenous and transplanted oysters. The most significant obstacle to developing effective treatment and management strategies for controlling *P. marinus* infections is the lack of a sensitive assay that would allow for both the detection of *P. marinus* at low infection levels and discrimination between putative geographic subpopulations of *P. marinus* as well as other Perkinsus species. There is a need for sensitive and specific diagnostic assays for *P. marinus* to detect, for example, cryptic infections in oyster seed-stocks, latent infections in overwintering oyster populations, the onset of infection in oyster larvae and spat, the presence of *P. marinus* in other marine organisms that may serve as secondary vectors or reservoirs, and the genetic structure of parasite field populations.

The life cycle of *P. marinus* within the host consists of an intracellular vegetative state (trophozoite) which proliferates by multiple fusion and/or budding. Mature trophozoites enlarge to become prezoosporangia, which upon entering the water column sporulate to release large numbers of biflagellated zoospores. These motile zoospores presumably give rise to trophozoites once they infect oyster tissue, but the mechanism of infection is unknown. With most prior art detection methods only trophozoites can be detected in most host tissues but not the other stages. It would be desirable to have an assay that is sensitive enough to detect any *P. marinus* life stage present in a sample.

Histology was the first technique used for diagnosis of *Perkinsus marinus*. The fluid thioglycollate media (FTM) assay (Ray,1952,1966) which has been the routine method for Perkinsus species diagnosis was adopted because it was inexpensive and simple to perform. In the FTM assay oyster tissue is incubated with antibiotic-fortified medium under conditions in which parasites at the trophozoite stage enlarge into hypnospores. These stain with Lugol's iodine solution for visualization of the parasite as a blue-dark sphere (Ray, 1966). The FTM assay relies on the enlargement of the trophozoites into hypnospores in fluid thioglycollate medium, a feature shared by all Perkinsus species and so does not distinguish between them. Hence this assay is not species specific. Consequently, most studies on Perkinsus from bivalves refer to them as Perkinsus species because no specific identification is possible. In addition, this assay is only able to detect one stage in the lifecycle of these parasites and takes between 4 and 7 days to complete. Hence, effective diagnosis in terms of sensitivity, species-specificity, and rapidity are needed for appropriate management of bivalve resources.

Antibody-based assays for the detection of *P. marinus* proteins in oyster tissues have recently been used with mixed success due to lack of sensitivity (Choi et al., 1991; Dungan and Roberson, 1993). These antibodies were raised against only one life stage of this parasite. Consequently the lack of sensitivity may be due to changes in epitope expression by the parasite at different life cycle stages. Also, a general feature of parasites is their ability to modify their epitope expression over time making an antibody-based assay unreliable. Because of these disadvantages, this technique never became established as a routine diagnostic assay for Perkinsus.

The sensitivity of PCR for detection of trace quantities of foreign DNAs in heterogenous samples has made this technology an ideal choice for identifying infectious agents and has been used with great success to screen protozoan pathogens in aquaculture (Cai et al., 1992; Stokes and Burreson, 1995). Different gene regions have been used as PCR targets. The ability of a PCR assay targeting DNA to distinguish between genetically related species and subspecies depends on the correct choice of a gene target. Fong et al. (1993) suggested the use of the small subunit of the rRNA gene of Perkinsus to design probes for this parasite, however this region cannot be used as a PCR target because the high degree of sequence identity that exists in homologous genes among between this parasite and its host.

The introduction and transplantation of shellfish has contributed to the spread of disease. The Working Group on Diseases of the International Council for the Exploration of the Seas (ICES) has established criteria for the introduction of exotic species as well as for transferred species. These criteria require periodic inspection and testing of the material using state of the art techniques before the mass transplantation and during quarantine. In addition, a significant obstacle to developing effective treatment and management strategies for controlling P. marinus infections in oysters is identifying when exactly an infection begins and the source of the pathogen. The only diagnostic technique routinely used up to this point has been the FTM assay which, as described, lacks the necessary requirements of sensitivity and specificity in detection of the parasite in order to help guarantee disease-free oysters.

There is a strong need, therefore, for a diagnostic assay that is (1) sensitive enough to detect the presence of the various species of Perkinsus at low levels, and (2) specific enough to discriminate between putative geographic races or strains of P. marinus and between the various species of Perkinsus, and (3) that can be completed rapidly enough to provide resource managers with timely information about the disease status of oyster populations, especially of oysters proposed for introduction from distant sources.

SUMMARY OF THE INVENTION

The present invention is directed to oligonucleotides used as amplification primers and assay probes for species-specific detection and identification of the protozoan Perkinsus in shellfish. The oligonucleotides are designed to preferentially hybridize to what has been found to be a species-unique sequence in the target organism's genome. Preferential hybridization means, for example, that the inventive primers amplify the target sequence in P. marinus with little or no detectable amplification of target sequences of other species of protozoa such as P. atlanticus thereby making the assay species specific.

The polymerase chain reaction ("PCR") and other probe based assays require a specific DNA sequence as a target. In diagnostic applications it is desirable that the DNA target sequence have a high copy number so as to increase the likelihood of detection at low levels of infection. Most organisms contain multiple copies of the genes that code for the ribosomal RNAs ("rRNA"). Usually RNA genes are organized in clusters comprising the following sequences shown schematically in FIG. 1: 5.0S gene, nontranscribed spacer ("NTS"), small subunit ("SSU") gene, internal transcribed spacer 1 ("ITS1"), 5.8S gene, internal transcribed spacer 2 ("ITS2"), and large subunit ("LSU") gene. The NTS separates transcription units but is not represented in the mature RNA products. Although this part of the molecule may not be important in terms of virulence or parasite proliferation, it is used, in accordance with the present invention, as a marker to distinguish between species and types. Coding regions of the rRNA genes are evolutionarily conserved, whereas the NTS is more variable and can differ significantly between even closely related species. The amplification primers and probes of the invention are based on the NTS domain of P. marinus and other species of this genus.

Since each eukaryotic microorganism has its own unique, species specific NTS sequence, the assay according to the present invention can be used to detect the genomic "fingerprint" of any target microorganism in a sample being tested. In short, to create an assay for a particular microorganism one needs to (i) isolate and sequence the NTS region for that species, and (ii) design an oligonucleotide probe or primers that will preferentially hybridize to the unique NTS.

These techniques were employed in the examples provided herein to identify the sequences of P. marinus and two other species of Perkinsus. Primers were then designed for each of these NTS and a PCR based assay was conducted on tissue removed from shellfish. The assay succeeded in detecting P. marinus in shellfish tissues and body fluids thereby providing valuable information about infection status. By using the primers disclosed herein in PCR amplification, genetic variability within P. marinus can also be detected. Distinction between two different types of P. marinus DNA has been discovered. We refer to these types as Type I and Type II. The specific primers indicated in Table 2 are PM5/PM7 for amplification of P. marinus Type I and PM6/PM8 for amplification of Type II. In our tested samples we repeatedly find Type I and Type II DNA and therefore these primers constitute the preferred method for determination of the presence of P. marinus.

The inventive assay has distinct advantages over the routine methods used presently. This assay can be performed in several hours rather than the 4 to 7 days required of prior art assay. The inventive assay is expected to become even more rapid as DNA technology improves. Another advantage is that the assay is sensitive enough to detect even a single parasite cell.

The assay according to the present invention thus provides (a) a rapid and economical assay that can be implemented in most labs with little in the way of specialized equipment; (b) a species-specific assay that can provide genetic lineage information about a particular Perkinsus sample; and (c) a sensitive assay for the detection of Perkinsus in tissues, body fluids, spat, and environmental samples. The inventive assay is also useful, for example, in helping marine biologists learn how P. marinus infects C. virginica because treatment approaches are dependent on identifying the life stage of the oyster that is the most susceptible to parasite entry and whether C. virginica populations are challenged by one continuous population of P. marinus or by discreet geographical races in order for management strategies to be implemented for regional areas infected by discrete P. marinus populations.

In a preferred embodiment the assay incorporates the PCR for the detection of DNA from P. marinus in oyster tissues. It has been found to be both sensitive enough to detect the presence of P. marinus at low levels in juvenile oysters and spat and specific enough to discriminate between different geographic races or strains of P. marinus. The invention may be employed both in commercial aquaculture as well as in areas of marine biology research where sensitive and reliable detection method are crucial in studying the etiology of diseases in populations of oysters and other shellfish.

The amplified DNA target provides sequence information of the genome and can therefore be secondarily employed to distinguish between related genetic strains of a pathogen if the DNA target region is carefully selected.

The assay according to the present invention has been employed to distinguish two sequence types of P. marinus. This variability may reflect different P. marinus types or races as well as a new way to define the parasite distribution. Two new sets of primers were developed based on the difference between the P. marinus types found. The primers serve as tools for a PCR reaction specific for the two types of P. marinus.

It is believed that the persistence of P. marinus in areas of the East coast where the salinity is low may reflect the existence of P. marinus races tolerant to low salinity. Hence the assay according to the present invention also provides valuable information about aspects of P. marinus types that helps marine biologists understand why one type prevail over the other in one particular area. Parasite genotypes and phenotypes may also reflect a different host susceptibility to the parasite. Hence, characterization of Perkinsus types would permit to improve the management strategies because a more effective control of the pathogen could be established for each particular region depending the parasite type more prevalent.

With the foregoing and other objects, advantages and features of the invention that will become hereinafter apparent, the nature of the invention may be more clearly understood by reference to the following detailed description of the invention, the appended claims and to the several views illustrated in the figures.

BRIEF DESCRIPTION OF THE DRAWINGS

FIG. 2 is the nucleotide sequence of the nontranscribed space (NTS) from *Perkinsus marinus*.

FIG. 3 is the nucleotide sequence of the NTS from a second species of Perkinsus isolated from *Macoma balthica*.

FIG. 4 is the nucleotide sequence of the NTS from a third species of Perkinsus isolated from *Mercenaria mercenaria*.

FIG. 5 lists representative sets of primers used for diagnosis of *Perkinsus marinus*, Perkinsus species number 2, and primers for *Perkinsus marinus* typing.

FIG. 10 is a ribosomal DNA nucleotide sequences of the non-transcribed spacer (NTS) domain from *Perkinsus marinus* Type I and Type II. Nucleotides shown in boldface indicate differences between P. marinus types.

REFERENCES

Figure 1:
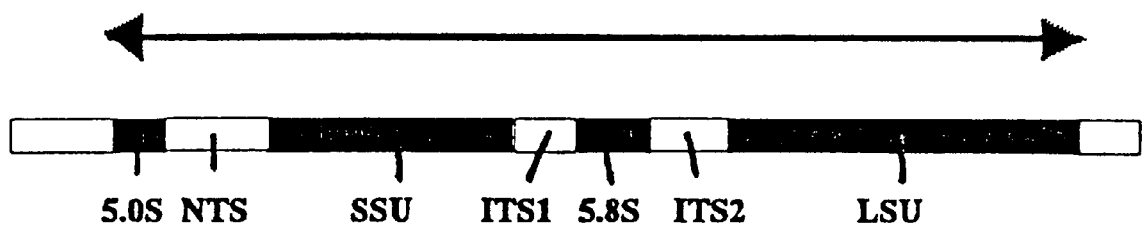
FIG. 1 is a schematic diagram of an rRNA gene cluster.

Ausubel, F. M., R. Brent, R. E. Kingston, D. D. Moore, J. G. Seidman, J. A. Smith and K. Struhl (eds.). 1992. Short Protocols in Molecular Biology, 2nd Edition. John Wiley and Sons, NY.

Cai, J., Collins, M. D., McDonald, V., and Thompson, D. E. 1992. PCR Cloning and Nucleotide Sequence Determination of the 18S rRNA Genes and Internal Transcribed Spacer I of the Protozoan Parasites *Cryptosporidum parvum* and *Cryptosporidium muris*. Bioch. Bioph. Act. 1131:317–320.

Choi, K. S., D. H. Lewis, E. N. Powell, P. F. Frelier, and S. M. Ray. 1991. A polyclonal antibody developed from *Perkinsus marinus* hypnospores fails to cross react with other life stages of P. marinus in oyster (*Crassostrea virginica*) tissues. J. Shellfish Res. 10: 411–415.

Dieffenbach, C. W. and Dveksler, G. S. 1995. PCR Primer: A Laboratory Manual. Cold Spring Harbor Laboratory Press, New York.

Dungan, C. F. and B. S. Roberson. 1993. Binding specificities of mono- and polyclonal antibodies to the protozoan oyster pathogen *Perkinsus marinus*. Dis. aquat. Org. 15: 9–22.

Fong, D., R. Rodriguez, K. Koo, J. Sun, M. Sogin, D. Bushek, D. T. L. Littlewood, and S. Ford. 1993. Small subunit ribosomal RNA gene sequence of the oyster parasite *Perkinsus marinus*. Molecular Marine Jbiology and Biotechnology 2: 3436–350.

Goggin, C. L. 1994. Variations in the Internal Transcribed Spacers and 5.8S Ribosomal RNA from Five Isolates of the Marine Parasite Perkinsus (Protista, Apicomplexa). *Mol. Biochem. Parasitol.* 65:179–182.

Innis, M., D. Gelfand, J. Sninsky and T. White (eds.). 1990. PCR protocols: A guide to methods and applications. Academic Press Inc., New York, N.Y.

Mackin, J. G. 1962. Oyster disease caused by *Dermocystidium marinum* and other microorganisms in Louisiana. Publ. Inst. Mar. Sci. Univ. Tex 7: 132–229.

Marsh, A. G., J. D. Gauthier, G. R. Vasta. 1995. A semi-quantitative PCR assay for assessing *Perkinsus marinus* infections in the eastern oyster, *Crassostrea virginica*. *J. Parasitol.*, 81: 577–583.

Perkins, F. O. 1996. Forward. *J. Shellfish Res.* 15:5–7.

Ray, S. M. 1966. A review of the culture method for detecting *Dermocystidium marinum,* with suggested modifications and precautions. Proc. Natl. Shellfish. Assoc. 54: 55–69.

Sambrook, G., Fartsch, E. F., Maniatis, T. 1989. *Molecular Cloning, A Laboratory Manual,* Second Edition. Cold Spring Harbor Laboratory, cold Spring Harbor, N.Y.

Sindermann, C. J. and Lihgtner, D. V. 1988. Disease Diagnosis and Control in North American Marine Aquaculture. Elsevier, N.Y., 431 pp.

Stokes, N. A. and Burreson, E. M. 1995. A Sensitive and Specific DNA Probe for the Oyster Pathogen *Haplosporidium Nelsoni*. *J. Euk. Microbiol.* 42: 350–357.

Sykes, P. J., S. H. Neoh, M. J. Brisco, E. Hughes, J. Condon, and A. A. Morley. 1992. Quantitation of targets for PCR by use of limiting dilution. Biotechniques 13: 444–449.

DETAILED DESCRIPTION OF THE INVENTION

A. Definitions

The following terms are defined herein as follows:

"DNA amplification" as used herein refers to any process which increases the number of copies of a specific DNA sequence. A variety of processes are known. One of the most commonly used is the Polymerase Chain Reaction (PCR) process of Mullis as described in U.S. Pat. Nos. 4,683,195 and 4,683,202 both issued on Jul. 28, 1987. In general, the PCR amplification process involves an enzymatic chain reaction for preparing exponential quantities of a specific nucleic acid sequence. It requires a small amount of a sequence to initiate the chain reaction and oligonucleotide primers which will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed. In the present invention the amplification results in an extension product of one sequence localized between two genes. Since these genes are multiple copy and the sequence target is between each copy, there will be exponential amplification for each of the copies. The extension products sizes using discrete primers will provide a specific fingerprint for each microorganism.

"Primer" means an oligonucleotide comprised of more than three deoxyribonucleotide used in amplification. Its exact length will depend on many factors relating to the ultimate function and use of the oligonucleotide primer, including temperature, source of the primer and use of the method. The primer can occur naturally (as a purified fragment or restriction digestion) or be produced synthetically. The primer is capable of acting as an initiation point for synthesis, when placed under conditions which induce synthesis of a primer extension product complementary to a nucleic acid strand. The conditions can include the presence of nucleotides and an inducing agent such as a DNA polymerase at a suitable temperature and annealing and extension times as well as the appropriate buffer (pH, magnesium chloride ($MgCl_2$) and potassium chloride ($KCl_2$) concentrations, and adjuncts). In the preferred embodiment the primer is a single-stranded oligodeoxyribonucleotide of sufficient length to prime the synthesis of an extension product from a specific sequence in the presence of an inducing agent. In the present application in the preferred embodiment the oligonucleotides are usually between about 10 mer and 35 mer. In the most preferred embodiment they are between 17 and 24 mer. Sensitivity and specificity of the oligonucleotide primers are determined by the primer length and uniqueness of sequence within a given sample of a template DNA. Primers which are too short, for example, less than 10 mer may show non-specific binding to a wide variety of sequences in the genomic DNA and thus are not very helpful. Each primer pair herein is selected to be substantially complementary to the different strands of each specific NTS region to which the primer pairs bind. Thus one primer of each pair is sufficiently complementary to hybridize with a part of the sequence in the sense strand and the other primer of each pair is sufficiently complementary to hybridize with a different part of the same repetitive sequence in the anti-sense strand.

"Oligonucleotide" as used herein means any nucleotide of more than 3 bases in length used to facilitate detection or identification of a target nucleic acid, including primers.

"Species-specific" means detection, amplification or oligonucleotide hybridization in a species of organism or a group of related species without substantial detection, amplification, or oligonucleotide hybridization in other species of the same genus or species of a different genus.

"Stringent annealing conditions" means that in those conditions the specificity, efficiency and fidelity of the PCR amplification will generate one and only one amplification product that is the intended target sequence.

"Nontranscribed spacer" or "NTS" are sequences that separate different portions of the rRNA at the level of the gene. The NTS are typically located between the genes that code for the 5.0S and the Small Subunit (SSU). (FIG. 1).

"Hybridize" or "Preferentially Hybridize" means the joining of two single stranded nucleotide sequences that are about 80% or more complementary.

B. Methods of Making Oligonucleotides

To create an assay for a particular species of microorganism one needs to (i) isolate and sequence the NTS region for that species, and (ii) design an oligonucleotide probe or primers that will preferentially hybridize to the unique NTS.

More particularly, to isolate and sequence an NTS region for a target species the following steps would be employed. First, it is determined whether the 5.0S and small subunit rRNA sequences for the species have been published in either the scientific literature or databases such as GEN-BANK. If so, using this sequence information, PCR primers are designed which hybridize to the rRNA genes flanking the NTS sequence using techniques known in the art (such as those described *PCR Primer: a Laboratory Manual* (Dieffenbach et al. 1995). The NTS is then amplified. Depending on the particular primer sequences selected, the best PCR conditions (annealing temperatures, pH, adjuncts, extension times, cycle numbers, salt concentrations) can be determined using any of a variety of commercially available computer programs such as GENE JOCKEY™ II (Biosoft, Ferguson, Mo.). Amplified products are resolved by agarose gel electrophoresis in the presence of ethidium bromide, recovered from the gel, and cloned into a commercially available cloning vector system (pGEM-T Vector, Promega, Madison, Wis.). Recombinant plasmids are transformed into competent cells and selected following the manufacture's protocol. Isolation of plasmid DNA is carried out using the method of Sambrook et al. (1989). For each PCR product, several clones with inserts are sequenced to confirm the sequence using an available DNA sequencing method (Applied Biosystems 373 DNA Sequencer, Perkin Elmer, Foster City, Calif.).

Alternatively, universal primers can be used to amplify the rRNA genes and the PCR products used to screen a genomic library (Sambrook et al.,1989) to pull out clones containing part of the entire NTS sequence.

After the NTS is sequenced, PCR primers specific for the NTS may be designed with assistance of commercially available computer programs such as GENE JOCKEY™ II (Biosoft, Ferguson, Mo.). The criteria for selecting the region to be amplified within the NTS are the following: length, sequence composition and melting temperature, and the ultimate applications, as will be readily known to those skilled in the art. The length of the region of the NTS that is selected to be amplified depends on the PCR primers selected. This length can be from 50 bp to full length, but is preferably from about 100 bp to 1200 bp, and optimally between about 250 and 600 bp. PCR conditions (annealing temperatures, pH, adjuncts, extension times, cycle numbers, salt concentrations) are determined following prescribed protocols in standard manuals such as *PCR Primer: a Laboratory Manual* (Dieffenbach et al. 1995). Primer lengths can be between 10 and 35 bases long, are preferably between 15 to 25 bases long, but most preferably will be between 17 and 24 bases long. Primers are tested against the target organism, related species, and the host in the case of a parasite. Sensitivity can be determined using different dilutions of target DNA for the PCR assay. General information about PCR and the design of primers not described herein may be found in Sambrook et al. (1989).

According to the method of the present invention, the liquid mixture is used in the amplification cycle of the PCR method. The amplification cycle comprises steps of: (i) denaturing a double-strand DNA (for about 10 seconds to 2 minutes at about 90° C., to 95° C.) (ii) annealing the single-strand DNA with the first and second primers (for about 30 seconds to about 3 minutes at about 37° C. to 70° C., and (iii) extending a DNA by the DNA polymerase (for about 30 seconds to about 5 minutes at about 65° C. to 80° C.). In the present invention the above mentioned amplification cycle is repeated 10 to 60 times, preferably 20 to 40 times. In the final cycle it is preferable to extend the heating time of the step (iii) to about 5 to 10 minutes so as to complete the DNA synthesis.

As described in the following Examples, the sequence of NTS region from an axenic culture of *Perkinsus marinus* has been cloned and sequenced and is shown in FIG. 2. Oligonucleotide primers to this DNA clone and evaluated their performance in detecting *P. marinus* infections in oyster tissues. Some details of our method may be found in the Publication, "A Semiquantitative PCR Assay for Assessing *Perkinsus Marinus* Infections in the Eastern Oyster, *Crassostrea Virginica*," 1995, *Journal of Parasitology* 81(4): 577–583, which is incorporated herein by reference. In this study, a 3.2 Kbp genomic clone of *P. marinus* was isolated and sequenced. A non-coding domain was identified and targeted for the development of a semiquantitative, polymerase chain reaction (PCR) assay for the presence of *P. marinus* in eastern oyster tissues. The assay involves extracting total DNA from oyster hemolymph and using 1 $\mu$g of that DNA as template in a stringent PCR amplification with oligonucleotide primers that are specific for the *P. marinus* NTS fragment. With this assay, it can detect 10 pg of total *P. marinus* DNA per 1 $\mu$g of oyster hemocyte DNA with ethidium bromide (EtBr) staining of agarose gels, 100 fg total *P. marinus* DNA with Southern Blot autoradiography, and 10 fg of total *P. marinus* DNA with dot blot hybridizations. This sensitive PCR assay has resulted in a method for estimating the level of *P. marinus* DNA in oyster hemolymph and it has been successfully applied to oyster gill tissues. The semiquantitative assay uses a dilution series to essentially titrate the point at which a *P. marinus* DNA target is no longer amplified in a sample. We refer to this technique as 'Dilution EndPoint' PCR. Using hemocytes obtained by withdrawing a 1 ml sample of hemolymph, this assay provides a non-destructive methodology for rapidly screening large numbers of adult oysters for the presence and quantification of *P. marinus* infection levels. Furthermore, we have now validated the PCR assay with field samples. When comparing PCR assay with the FTM assay the PCR technique is more sensitive and faster. Comparison of FTM and the PCR assays for *Perkinsus marinus* diagnosis showed that in 83% of the samples there was agreement between FTM and PCR analysis. Detailed analysis of the discrepancies showed that 15% of all samples were negative by FTM but positive by PCR analysis, while only 2% of the samples were FTM positive but were not amplified by PCR. The FTM−/PCR+ discrepancy may be attributed to a greater sensitivity of the PCR methodology. Using the same methodology *P. marinus* has been detected in four species of non-oyster bivalves in Chesapeake Bay. Consequently, this technique is applicable to other oyster and bivalve tissues (gills, mantle, rectum) and could potentially be applied to DNA extracts of whole larval or spat as well as sediment and water samples.

In a preferred embodiment sets of primers are used in PCR amplification. These sequences are derived from the nontranscribed sequence between the 5S and SSU rRNA genes of *P. marinus*. The entire nontranscribed sequence is shown in FIG. 2. Additional primers, of lengths greater or less than those described here, derived from this sequence could also function in the diagnostic test for *P. marinus* described herein.

C. Using the Assay

To conduct the assay a DNA sample is extracted from any tissue or body fluid of the shellfish. DNA is extracted using conventional techniques such as described in Sambrook et al. (1989). Target DNA is amplified by adding a pair of outwardly-directed primers (made as described above), wherein the primers can hybridize to the NTS sequences, separating the extension products generated in the amplification step by size, and the specific species and strain of Perkinsus determined by sequence or enzymatic digestion of the extension products.

In addition to the PCR-diagnostic assay, the NTS region can be used to develop a quantitative PCR assay retaining specificity that will permit the accurate assessment of the numbers of *P. marinus* in tissue and hemolymph of infected oysters. For a number of applications and studies, it is essential to determine accurately the number of parasites in different samples. Competitive PCR offers a precise method for determination of the concentration of target molecules which can than be calibrated to calculate cell number. The basis for competitive PCR is the design of a competitor template whose product can be distinguished from experimental template but at the same time is extremely similar in its composition. This competitor template is added to the PCR reaction is known quantities and co-amplified with sample DNA and the ratio of known amount of competitor product to experimental product can be used to determine the DNA concentration of the experimental template and correlate the amount of template produced with a standard cell number. Kits available on the market (PCR Mimic System, Clontech, Palo Alto, Calif.) can be used to construct competitive fragments for quantitative PCR.

Since the NTS region has resulted in the ideal choice for diagnostic intent, a series of techniques now available can be applied using this region as a base; for example, in situ detection of PCR-amplified DNA. This technique combines the cell localizing ability of in situ hybridization with the extreme sensitivity of PCR. Although PCR is a faster technique than FTM, significant reduction of time can be achieved by adapting the capillary PCR. This technique uses capillary tubes instead of microfuge tubes in combination with Rapidcycler (Idaho Technology) and PCR that usually takes between 2–4 hours can be reduced to 15 minutes. Partial or complete, the sequence of the NTS can be labeled for detect, quantitate and isolated specific polynucleotides. Both radioactive and nonradioactive labeling methods using $^{32}P$, $^{35}S$, biotin and dioxigenin are suitable to label the probe.

The method according to the present invention may be used to detect and distinguish among most species of organisms (pathogens or non-pathogens). In the examples herein the NTS is used to develop a PCR-based assay for several different Perkinsus species affecting oysters and clams. These NTS sequences are shown in FIGS. 2–4. It has been shown that the clams (*Macoma balthica* and *Mercenaria mercenaria*) harbor both *Perkinsus marinus* and Perkinsus species that are not *P. marinus*. This situation may also occur in oysters where parasite presence is usually assessed by either FTM assay or morphology, two techniques that do not permit specific identification of Perkinsus. The NTS regions of the Perkinsus species affecting clams have been completely sequenced and the sequence used for developing new specific primers for these Perkinsus isolates or species that will allow us to distinguish between these isolates and establish whether oysters have been exposed to multiple Perkinsus species infections. Other future uses include the employment of the NTS for developing a diagnostic assay for *Vibrio vulnificus,* a serious human pathogen that oysters, as filter feeders, can accumulate in their tissues.

In a preferred embodiment five sets of primers are used in PCR amplification (FIG. 5). The entire nontranscribed sequences of Perkinsus species number 2 from *Macoma balthica* and Perkinsus species number 3 from *Mercenaria mercenaria* are shown in FIGS. 3 and 4. Additional primers, of lengths greater or less that those described here, derived from this sequence could also function in the diagnostic test for Perkinsus species described herein.

A further embodiment of the present invention is a machine for identifying a strain of pathogen comprising an automated PCR amplifying means, a separation means, a sampling means for removing the extension products from the PCR means and transferring them to the separation means, a reading means for measuring patterns of extension products after separation of the separation means, a computer means for recording the results of the reading means and for outputting the pattern of and identifying the strain of the microorganism.

A number of automated PCR amplifying means are known on the market. For instance a thermal cycler can be used. There are a number of arms or robotic devices and other automatic pipette and sampling machines which can be used as a sampling means for removing the extension products from the PCR reaction at the appropriate times and transferring the sample for either chromatography, gel or capillary electrophoresis, mass spectrometry or other methods or techniques used separate the samples. In the preferred embodiment the separator means is regulated by the computer. After the separation the reader means is used to measure the pattern. The reader means will depend on the type of separation which is being used. For instance a wavelength densitometer reader or a fluorescence reader can be used depending on the label being detected. A radioisotope detector can be used for radioisotope labeled primers. In mass spectrometry the ions are detected in the spectrometer. A gel can be stained and read with a densitometer. The computer regulates the automated PCR amplification procedure, the sampling and removal from PCR, the automatic separation and reading of the samples and can be used to interpret the results and output the data.

The products, methods, instruments and procedures described herein can be used for a variety of purposes. Because of the sensitivity and specificity of the test one skilled in the art will readily recognize uses for this methodology. What follows is not an inclusive list of uses but only a sampling of specific areas where a current need exists for a quick and reliable test.

One important use of the present invention is certification of disease-free larvae, spat and juvenile oysters. Although during the last 25 years a significant progress in understanding this disease has been done (Perkins, 1996), fundamental aspects of the life cycle remain unclear or unknown. Such is the case of which is the life stage of the oyster that is sensitive to the onset of this disease and which is the infective stage of *P. marinus* in natural conditions. Many parasites establish latent and persistent infections that may pose diagnostic dilemmas. One of the main strategies to avoid the spread of *P. marinus* is to transplant only disease-free oysters. During many years oyster managers have depended on movement of oyster from seed areas to growing areas in order to avoid the overcrowding and to distribute the harvest geographically. The PCR assay developed is a specific, sensitive and rapid method for certifying *P. marinus*-free oyster seed and juveniles. In addition it may provide a tool for better evaluating and predicting the condition of oyster stocks and beds.

Another important use of the present invention is a kit for detecting *P. marinus* and related species and strains. The specific primers described here can be incorporated into a kit for detection of *P. marinus* at various stages of oyster development. The rapid amplification of large numbers of samples may be analyzed to determine variation in population densities in environmental samples or to assay infection intensities from a large group of experimentally infected oysters. This kit preferably comprises a container having a pair of outwardly-directed PCR primers to the NTS region of the microorganism(s) being tested for. This kit can have any of the PCR primers listed in FIG. 5 or a combination thereof. One skilled in the art will readily recognize that the number and type of primers which are in the kit will depend on the use of the kit as well as the sequences to be detected. The kit would also include the buffers, DNA polymerase, and dideoxynucleotides, $KCl_2$ and $MgCl_2$ and all other reagents necessary to conduct PCR amplification. Also included would be instructions as to how to dilute the sample in preparation for "Dilution Endpoint" PCR analysis. Directions for performing the analysis by either dot blot or Southern blot hybridizations could also be included. The kit will include competitor template whose product can be distinguished from the experimental template but at the same time is extremely similar and competitor in preparation for competitive PCR.

The present invention can be used, for example, with oysters and associated invertebrate fauna from the Chesapeake Bay. The application of PCR methodology for the detection of the parasite in other shellfish species should provide information about the possibility that oysters from the Chesapeake Bay are infected by the same *P. marinus* type that may be present in putative reservoirs or alternative hosts. One example is *Macoma balthica* a bivalve that is abundant and easily obtained in the Chesapeake Bay. In addition, other organisms living on or near oyster reefs with a known with a known history of Perkinsus infection can be tested.

The invention may be used to evaluate the presence of *P. marinus* in the water column or sediments. Waterborne infection particles are expected to increase during the summer as temperature and salinity increase and oysters die from the disease dumping infective particles into the water column. With the PCR assay one can detect life stages which are undetectable and more accurately than with serological methods alone.

There are several approaches for applying nucleic acid probes to the detection of specific DNA or RNA sequences, but in developing suitable applications for *P. marinus*, we have selected biotechnological strategies to provide: a) a rapid assay that could be implemented in most labs with a minimum of specialized equipment; b) a species-specific assay that can be applied to any bivalve tissue for diagnostic purpose; c) a strain-specific assay that could provide genetic lineage information about a particular Perkinsus sample; d) a sensitive assay for the detection of *P. marinus* in tissues of oyster juveniles and spat, and e) the possibility to extend this diagnostic strategy for any Perkinsus species. The invention herein meets these objectives.

Any quantitative diagnostic assay requires a rigorously established detection limit. The sensitivity of the PCR assay was assessed through spike and recovery experiments using *P. marinus* cells in the presence of parasite tissue. The PCR-based diagnostic assay is able to detect as few as one cell in presence of 30–40 mg of oyster tissue.

From the agarose gels of Example 3b, it is apparent that there are distinct differences in the amplification intensity of the *P. marinus* DNA target. The most likely source of these differences is the amount of *P. marinus* DNA in each of the oyster sample DNA extracts. Most quantitative PCR strategies essentially involve some form of a competitive assay in which the amplification of a known template is used to calculate an efficiency that is subsequently used to convert the amplification of an unknown back to its starting template concentration (see Innis et al., 1990). These techniques all require a genetically engineered standard target and a thorough quantification of reaction kinetics.

In contrast, a semi-quantitative assay is used herein that can be performed on any sample without any prior preparation or standardization. It is based on identifying the lowest dilution at which the amplification of a specific target sequence is no longer detectable. Limiting dilution assays are routinely used for many cell biology applications, but only recently have such assays been developed for the detection sensitivity of PCR (Sykes et al., 1992). The accuracy of the assay is only as fine as the dilution level employed to titrate the Endpoint, but the precision in our samples is high and there appears to be no affect by the presence of significantly higher levels of oyster DNA. We refer to this technique as "Dilution EndPoint" PCR. Estimating an infection level to the nearest power of 10 may not appear to be an accurate measure, but it may provide the degree of quantification necessary to determine changes in oyster infection levels in response to experimental manipulations.

In summary, the present invention based on the NTS from sequence comprises a PCR-based diagnostic assay for the detection and quantification of *P. marinus* DNA in oyster and other bivalves DNA extracts. This technique provides a rapid and reliable assessment of *P. marinus* infection levels. The PCR assay establishes a new diagnostic procedure that provides a level of sensitivity and quantification that is not afforded by the FTM assay. This invention also comprises a PCR-based diagnostic assay for the detection of Perkinsus species. in bivalves DNA extracts.

EXAMPLES

The present invention will now be further illustrated by, but by no means limited to, the following Examples.

Example 1a

Design and Preparation of Primers (*Perkinsus marinus*)

Total DNA was extracted from axenic cultures of *P. marinus* using a standard SDS/proteinase-K protocol (Ausubel et al., 1992). From a BamHI endonuclease digestion, a 3.2 Kbp fragment was gel purified and cloned into the polylinker of pBluescript (Stratagene, La Jolla, Calif.). Both strands of this clone were sequenced using dideoxy terminators on an ABI automated DNA sequencer according to the manufacturer's instructions. Sequence analysis using both GCG-FASTA searches through GenBank and PAUP alignments revealed that the 3.2-kb clone encoded the 5S and SSU rRNA genes separated by a 1.1-kb non-coding domain. The development of a PCR-based assay for this DNA fragment focused on the sequence information of the non-coding domain between the two rRNA genes. Oligonucleotide primers were designed for this region using the PRIMER program (V0.5, Whitehead Institute, Cambridge, Mass.) with stringent criteria, including a requisite that their melting temperatures be above 58° C. The best pair of primers was the forward sequence 5'-CAC TTG TAT TGT GAA GCA CCC-3' and the reverse sequence 5'-TTG GTG ACA TCT CCA AAT GAC-3' which would amplify a 307 bp target region. These primers were synthesized on a Beckman Oligo1000 DNA synthesizer, quantified by optical density at 260 nm, and diluted to 100 $\mu$M working stock solutions with sterile water.

Oysters were obtained from three sources. One dozen oysters were purchased from Mook Sea Farms, Damariscotta, Me., to serve as negative (uninfected) controls. Fourteen oysters were obtained from two sites in Louisiana and shipped to us to serve as our primary field samples. We obtained nine DNA samples that had been prepared from oyster gill tissues from individuals collected at nine sites along the Gulf of Mexico and Atlantic seaboard. In addition, The DNA from the hemocytes of a heavily infected oyster from a previous study (stage 5 of the Mackin [1962] scale for the thioglycollate assay) was extracted for use in this study as a positive infection control.

Example 1b

Design and Preparation of Primers (Perkinsus spp.)

Total DNA was extracted from axenic cultures of Perkinsus spp. from *Macoma balthica* and Perkinsus spp. from *Mercenaria mercenaria* by adapting a spin-column methodology designs for the isolation of DNA from human tissues (Qiagen, Chatworth). Sample optical density at 260 and 280 nm was used to quantify the DNA concentration and assess the DNA quality. PCR primers flanking NTS sequences of *P. marinus* in the 5.0S and SSU rRNA gene (unpublished data) were used for amplification of the NTS region of the Perkinsus isolates. PCR reactions were performed following Goggin (1994) in a total volume of 25 µl using DNA Pelticer Thermal Cycler (MJ Research) and resolved on 1.5% agarose gel in the presence of ethidium bromide (EtBr, 10 ng/ml final concentration in the gel). PCR amplification products from *M. balthica* and *M. mercenaria* were cloned into pGEM-T Vector (Promega). Recombinant plasmids were used to transform JM 109 Competent cells and were selected on Xgal, IPTG, ampicillin, tetracycline LB plates, following the manufacture's protocol. Individual colonies were grown overnight in LB or Terrific borth and minipreps extracted using the Wizard, Plus Minipreps DNA purification System (Promega). For each isolate five clones with inserts were sequenced via the dideoxy chain termination method using the DNA Sequencing Kit (Perkin Elmer, Foster City, Calif.) in an Applied Biosystems 373 DNA Sequencer (FIG. 3 and FIG. 4). Oligonucleotide primers were designed for this region. The best pair of primers was the forward sequence 5'-AAG TCG AAT TGG AGG CGT GGT GAC-3' and the reverse sequence 5'-ATT GTG TAA CCA CCC CAG GC-3'.

Example 2a

Extraction and Purification of DNA (Oysters Tissue Samples)

Tissue samples are processed by adapting a spin-column methodology designed for the isolation of DNA from human blood samples (Quiagen, Chatworth, Calif.). The tissues are lysed in presence of sodium dodecyl sulfate (SDS), proteinase-K, and guanidinium HCl. The microscale extracts are passed through a column matrix than binds double strained DNA and washed several times with 60% buffered ethanol to remove any contaminating proteins and lipids. The DNA is eluted from the column with water in a volume of 50 HCl. Sample optical density at 260 nm is used to quantify the DNA concentration and samples are then diluted using sterile water to a final concentration of 1 µg total DNA (*Crassostrea virginica* and *Perkinsus marinus* DNA).

Example 2b

Extraction and Purification DNA (Oysters Hemolymph Samples)

A 1 ml sample of hemolymph was removed from the adductor muscle of each oyster through a notch in the shell. The hemocytes were pelleted in a microcentrifuge and then processed by adapting a spin-column methodology designed for the rapid isolation of DNA from human blood samples (Qiagen, Chatworth, Calif.). The hemocytes were lysed in the presence of SDS, proteinase-K and guanidinium HCl. The micro-scale extracts were passed through a column matrix that binds double stranded DNA and washed several times with 60% buffered ethanol to remove any contaminating proteins and lipids. In order to set up a diagnostic PCR assay, each reaction has to use a known amount of starting template and there are several significant advantages to adapting these separation columns to produce clean hemocyte DNA extracts: 1) they do not require the use of organic solvents (phenol and chloroform) that are required by standard extraction techniques, which dramatically reduces the handling time needed to prepare each sample; 2) RNA is removed from the sample so that a separate RNase digest is not required in order to quantitate the DNA on a spectrophotometer.

Example 2c

Extraction and Purification of DNA (Bivalve Tissue Samples)

Tissue samples are processed by adapting a spin-column methodology designed for the isolation of DNA from mouse tail or from tissue (Qiagen, Chatworth, Calif.). The tissues are lysed in presence of buffers and proteinase K. The micorscale extracts are passed through a membrane than binds double strained DNA and washed several times with buffered ethanol to remove any contaminating proteins and lipids. The DNA is eluted from the column with water in a volume of 50 µl. Sample optical density at 260 nm is used to quantify the DNA concentration and samples are then diluted using sterile water to a final concentration of 1 µg total DNA (Bivalve and parasite DNA).

Example 3a

Amplification of *P. marinus* DNA by PCR

All samples were subjected to identical reaction conditions for PCR amplification in an Ericomp Twin-Block, water cooled thermal cycler. A heat stable Taq DNA polymerase was purchased from Promega (Madison, Wis.) and each assay used 1.5 Units of enzyme in a 25 µl volume with the manufacturer's reaction buffer. In addition, each assay contained 1.5 mM $MgCl_2$, 200 uM each dNTP, 2 uM each primer and 1 µl (1 µg) of template DNA. The temperature profile for the amplification was 2' @ 94° C., 3' @ 61° C. and 2' @ 72° C. This temperature profile was repeated for 35 cycles. Each PCR run started with a 5' @ 94° C. denaturation and was completed with a 20' @ 72° C. extension. Alternative protocols were tested to include: more DNA polymerase, more amplification cycles, higher and lower annealing temperatures, higher primer concentrations, and higher starting template concentrations, but these did not increase the assay's detection efficiency. The conditions listed above were determined to be the optimum reaction characteristics.

Example 3b

Amplification of *P. marinus* DNA by PCR

Figure 6:
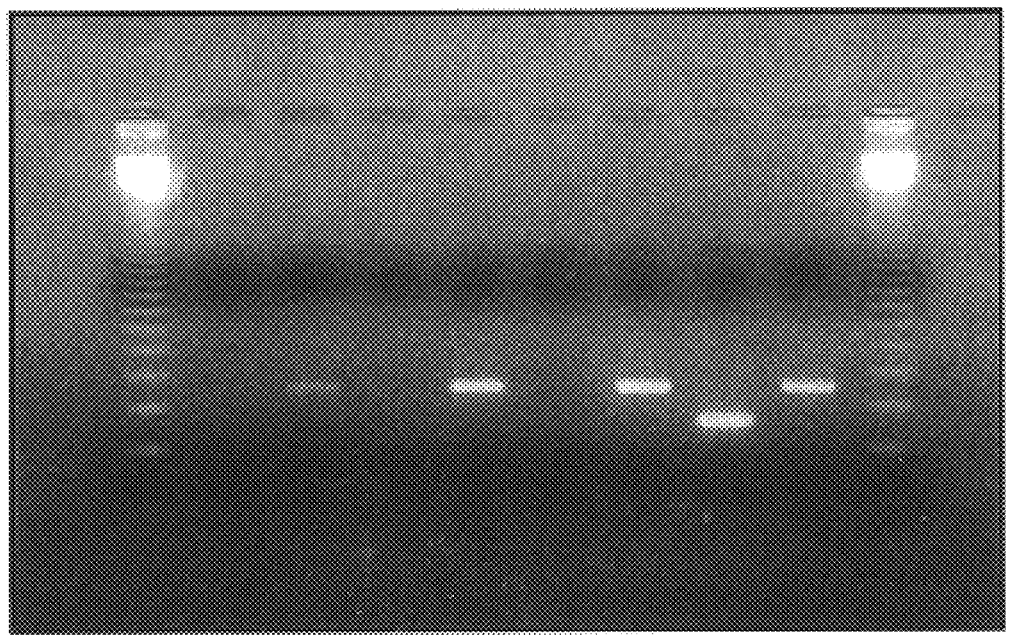
FIG. 6 is an agarose gel electrophoresis of amplified products of PCR demonstrating species-specificity of P. marinus diagnostic primers. Amplification of DNA with P. marinus diagnostic primers (d) only occurred with P. marinus samples. However, PCR with actin primers (a) amplified all samples. P. sp. (1) Perkinsus sp. from *Anadara trapezia*, P. o. P. olseni from *Haliotis laeviagata*, P.a. P. atlanticus from *Ruditapes decussatus*, P.m. P. marinus from *Crassostrea virginica*. M. 123 bp DNA ladder.
Figure 7:
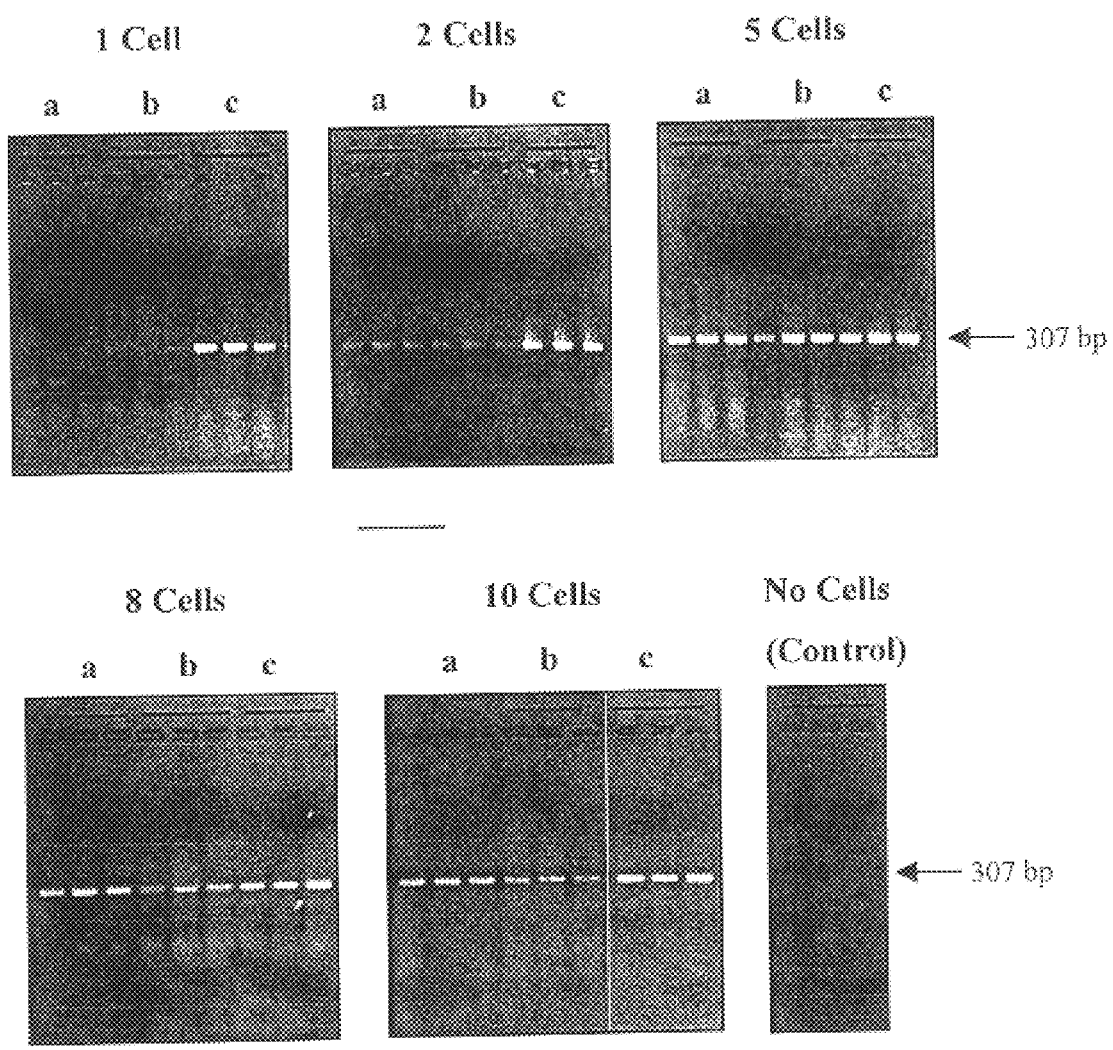
FIG. 7 are agarose gel electrophoresis of amplified products of PCR demonstrating the sensitivity of P. marinus diagnostic primers. Using this methodology as few as one cell was detected. Three samples (×3) were used for 1,2,5,8 and 10 cells.

PCR primers (5'-CAC TTG TAT TGT GAA GCA CCC-3', 300 F and 5'-TTG GTG ACA TCT CCA AAT GAC-3', 300 R) derived from a non transcribed space (NTS) domain of rRNA sequence from *P. marinus* will be used for *P. marinus* diagnosis (Marsh et al. 1995). PCR reaction mixtures contain reaction buffer (10 mM Tris, pH 9.2; 1.5 mM $MgCl_2$; 75 mM KCl; 0.02% Tween-20; 10 μM TMAC; 10 μg/ml BSA; 2.5% DMSO and 5% Formamide); 1 μM of each primer; 200 μM each dATP, dCTP, dGTP and dTTP; 1.5 units of Taq DNA Polymerase (Fisher Biotech) and 1 μg DNA template in a total volume of 25 μl. Samples are heated to 91° C. for 3 min and then the reaction mixtures are cycled in a DNA Peltier Thermal Cycler (MJ Research) 35 times at 91° C. for 1 min, 58° C. for 1 min (plus 1 sec/cycle), and 72° C. for 1 min (plus 2 sec/cycle) with a final extension at 72° C. for 10 min. PCR products are resolved on a 2% agarose gel in the presence of ethidium bromide (EtBr, 10 ng/ml final concentration in the gel) and using 1×TAE buffer. A repetitive 123 bp ds DNA size standard (Promega, Madison, Wis.) is included on the gels. DNA sequencing will be by direct sequencing from PCR products and/or by cloning into a vector. This PCR is species-specific (FIG. 6) and it is able to detect as few as one cell in the presence of oyster tissue (FIG. 7). In parallel, we can apply a different set of primers to amplify a 500 bp fragment from the NTS domain.

Example 3c

Amplification of Perkinsus Species DNA by PCR

Figure 8:
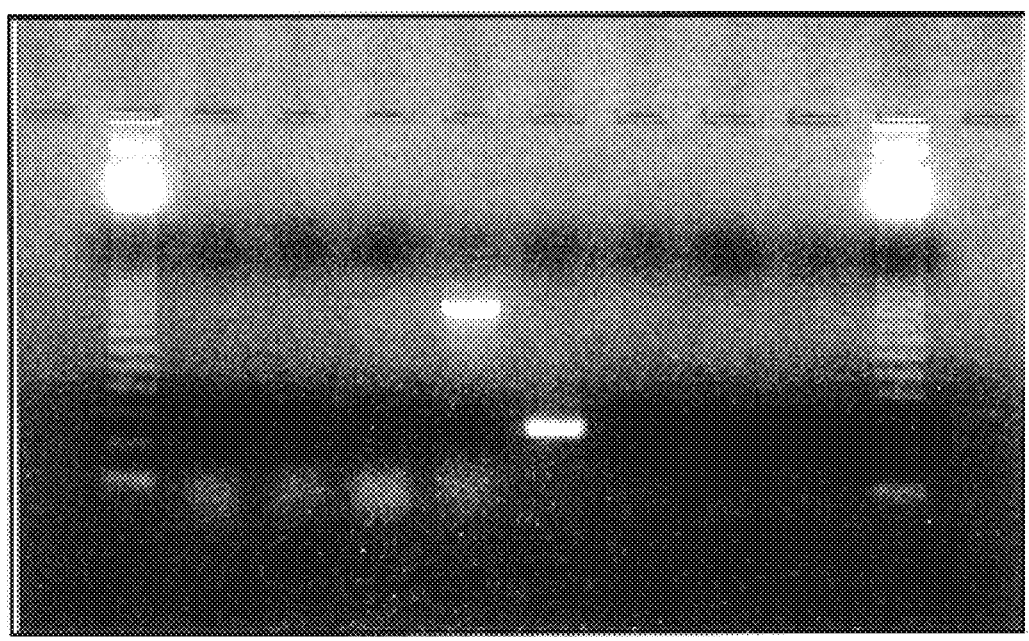
FIG. 8 is an agarose gel electrophoresis of PCR products of different Perkinsus isolates using P. marinus diagnostic primers (a) and primers derived Perkinsus sp. isolated *Macoma balthica* (b). 1. Perkinsus sp. from *Mercenaria mercenaria* 2. Perkinsus sp. from *Macoma balthica*, 3. P. marinus from *Crassostrea virginica*, 4. Negative controls, M. 123 bp DNA ladder.

PCR primers (5'-AAG TCG AAT TGG AGG CGT GGT GAC-3', A8-1 F, AND 5'-ATT GTG TAA CCA CCC CAG GC-3', A8-1 R) derived from a non-transcribed space (NTS) domain of rRNA sequence from Perkinsus spp. from *Macoma balthica* will be used for Perkinsus sp. diagnosis. PCR reaction mixtures contain reaction buffer (Fisher Biotech); 1 μM of each primer; 200 μM each dATP, dCTP, dGTP and dTTP; 1.5 units of Taq DNA Polymcrase (Fisher Biotech) and 1 μg DNA template in a total volume of 25 μl. Samples are heated to 94° C. for 4 min and then reaction mixtures are cycled in a DNA Peltier Thermal Cycler (MJ Research) 35 times at 91° C. for 1 min, 55° C. for 1 min (plus 1sec/cycle), and 72° C. for 1 min (plus 2 sec/cycle) with a final extension at 72° C. for 10 min. PCR products are resolved on a 1.5–2% agarose gel in the presence of ethidium bromide (EtBr, 10 ng/ml final concentration in the gel) and using 1×TAE buffer. A repetitive 123 bp ds DNA size standard is included on the gels (FIG. 8). Alternatively new sets of primers derived from the NTS domain may be used for amplification.

Example 4

Analysis of PCR Products

Figure 9:
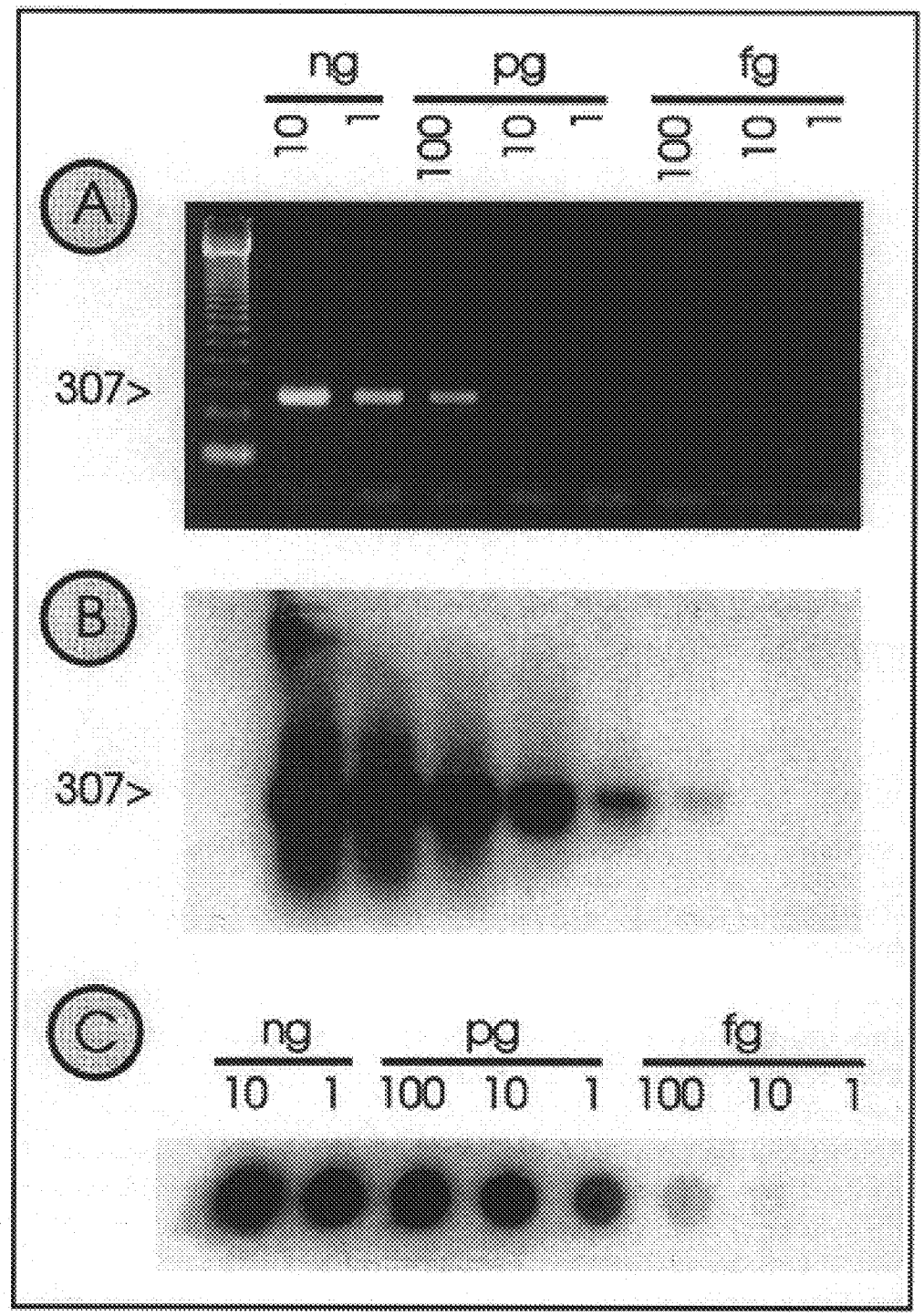
FIG. 9 is amplification of the Perkinsus marinus DNA target using a known amount of total P. marinus DNA in a 10×serial dilution with a constant level of oyster genomic DNA (1 $\mu$g/pl). A. Ethidium bromide visualization of the resolving gel. B. Southern blot of the above gel. C. Dot-blot hybridization of PCR amplification.

PCR products were resolved on a 1.5–2% agarose gel in the presence of ethidium bromide (EtBr; 10 ng/ml final concentration in gel) by loading 12.5 μl of the 25 μl reaction volume into each well. A repetitive 123 bp dsDNA size standard (Promega) was included on the gels (FIG. 9A). Gels were photographed and then denatured in 0.5N NaOH with 1.5M NzCl for 45 min, neutralized in 1M Tris-HCl (pH 7.2) with 1.5M NaCl for 45 min, and blotted on nylon membranes (Schleicher and Schuell, Keene, NH) by capillary transfer overnight (Ausubel et al., 1992). DNA on the nylon membranes was UV cross-linked and the membranes stored dry at room temperature. Membranes were prehybridized for several hours in 40% formamide, 25 mN Na-PO4 (pH 7.2), 5× standard saline citrates, 0.1% SDS, 5×Denhardt's and 50 μg/ml yeast RNA at 42° C. in a hybridization oven. A PCR amplified product with $cx^{32}P$-dCTP (3,000 Ci/mol), added to the hybridization tube with a fresh 10 ml aliquot of hybridization buffer (as above) and incubated overnight at 42° C. All PCR amplifications were first resolved on 2% agarose gels to ensure that spurius reaction products were not present (FIG. 9B). After this visual inspection, 12.5 μl aliquots of each PCR amplification were directly loaded onto nylon membranes using a dot-blot apparatus with gentle vacuum. The membranes were then denatured and neutralized as described for the agarose gels int he above section, and the DNA UV cross-linked. Hybridization conditions followed the procedure described above for the southern hybridizations (FIG. 9C).

Kodak Biomax film was used for all radiographic exposures because of the low background interference from having emulsion on only one side of the film. The oprimum length of time for exposing the film was between 12 and 24 hours with intensifying screens at 80° C. For grain densitometry, autoradiographs were digitized on a Microtek gray-scale scanner at 300 dpi and imported as TIFF files into Adobe Photoshop®. The Histogram routine in Photoshop® was used to estimate the average pixel value (white=0, black=225) for a gel band or dot-blot, which is here reported as autoradiograph grain density.

Example 5

Determination of *P. marinus* Types

Figure 11:
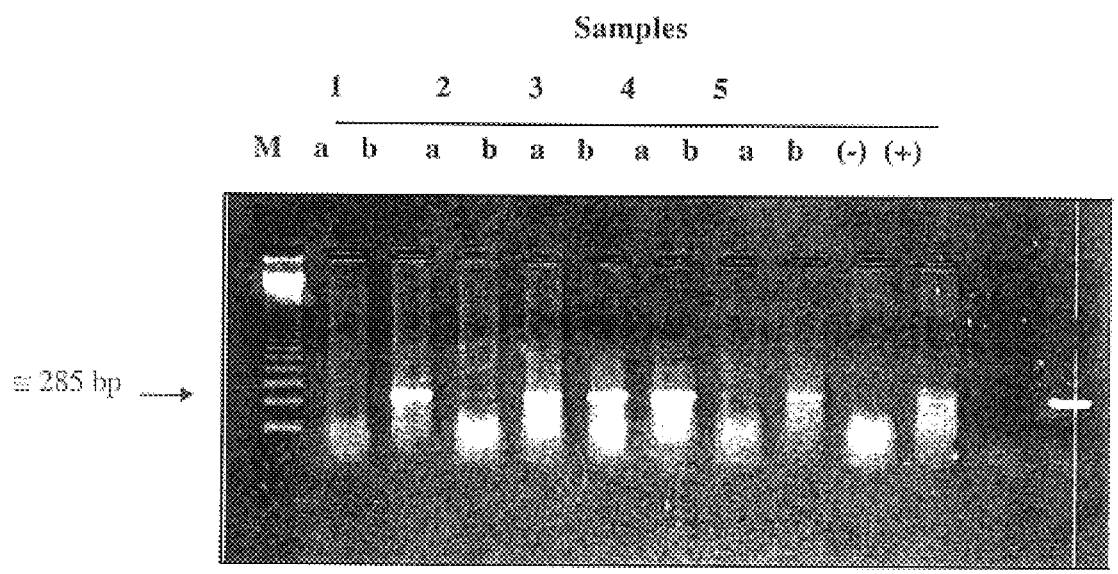
FIG. 11 is an ethidium bromide stained agarose gel electrophoresis of PCR products generated by amplification of DNA derived from oysters (*Crassostrea virginica*) infected with *Perkinsus marinus*. Lanes 1 to 5 using primers PM5/PM7 specific for P. marinus type 1 (lane a) and primers PM6/PM8 specific for P. marinus type II (lane b). M. 123 bp DNA ladder. (+) control P. marinus type II. Note the presence of bands corresponding to both Perkinsus types in the same oyster in samples #2 and #3.
Figure 12:
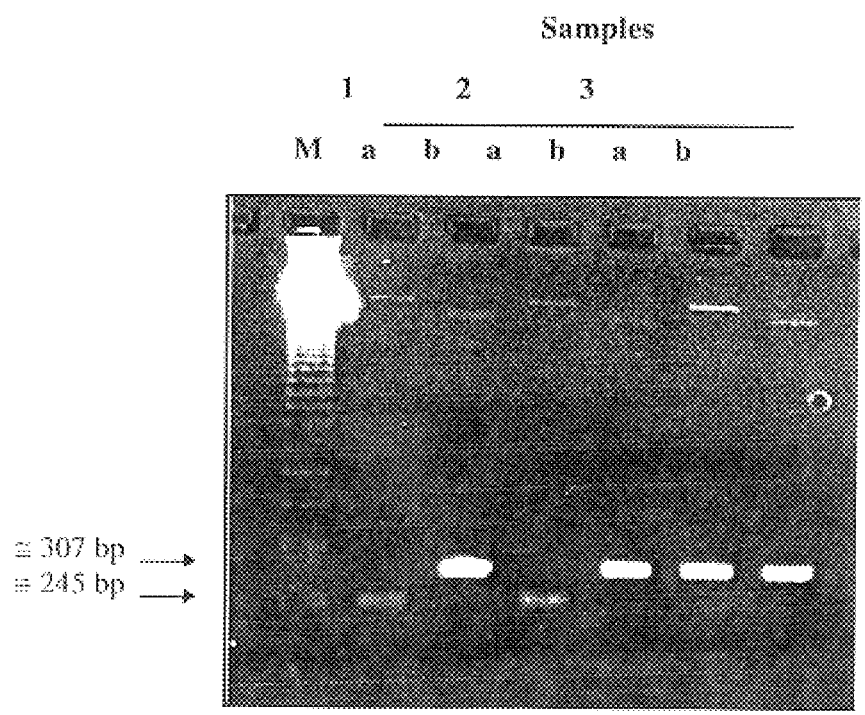
FIG. 12 is an agarose gel showing the patterns of *Perkinsus marinus* types after Spe1 digestion of PCR amplified products. P. marinus type I (samples #1 and #2) and P. marinus type II (sample #3). Sample with enzyme (lane a). Sample without enzyme (lane b).

In order to identify Perkinsus type, two methods of differentiation can be applied: (a) by PCR, using newly designed sets of primers with specific amplification of individual *P. marinus* types and (b) restriction mapping. PCR using the PM5/PM7 primers amplified *P. marinus* type I and PM6/PM8 primers amplifies *P. marinus* type II (FIG. 10) exclusively, thus establishing specificity of the primers. The PCR reaction mixture used with the new primers was as above (Example 3B). The annealing temperature was 60° C. instead of 58° C. as used for the PCR diagnostic assay in order to increase the specificity (FIG. 11). The original diagnostic primers (not type-specifies) produced a 307 bp PCR product digestable with SpeI in the case of Type I, whose sequence contains the restriction site, but not Type II, whose sequence does not hace the site. Restriction enzyme digestion was carried out using the SpeI (ACTAGT) enzyme. The enzyme mix was added to a final volume of 20 μl following the manufacture recommendations (GIBCOBRL) in the presence of 200 ng of PCR products. After 3 h of incubations at 37° C., the digested products were run on a 1.5% agarose gel in the presence of ethidium bromide to resolve digested PCR fragments. One band was 245 bp and the other 62 bp (FIG. 12). Consequently, both specific PCR and restriction digestion can be used in the future for *P. marinus* type identification. In vitro culture methods will permit investigation of other genes that probably are more relevant for the virulence and pathogenicity of *P. marinus*. Restriction maps will also permit the identification of specific regions of the *P. marinus* genome that vary between types and specific genes present in only one type, possibly relevant to virulence and pathogenicity.

Example 6

Distribution of *P. marinus* Types in Oyster Samples

Figure 13:
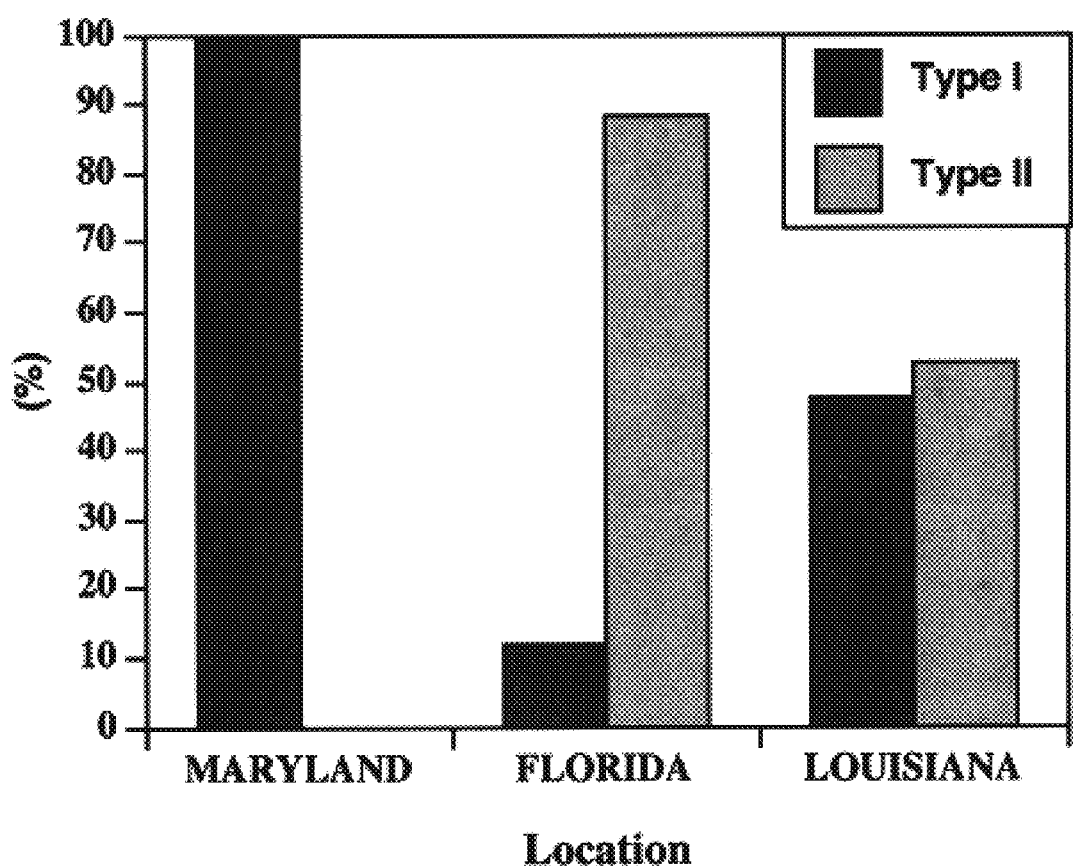
FIG. 13 is a chart showing the distribution of *Perkinsus marinus* types in samples form Maryland, Florida and Louisiana.

The use of the NTS domain from *P. marinus* rRNA gene to investigate the divergence between *P. marinus* affecting *Crassostrea virginica* has yielded the following results: 1) both types were found (types I and II) in the studied oysters (FIG. 10). 2) interestingly, the isolates from the sampled areas (Maryland, Florida and Louisiana) showed different frequencies for the *P. marinus* types (FIG. 13). We suggest that this variability may reflect different *P. marinus* types or races as well as a new way to define the parasite distribution. We are currently identifying genetic polymorphisms in *P. marinus* population structure along the Gulf of Mexico and the Atlantic seaboard. We will be able to discern whether or not the genetic discontinunities that may characterize oyster populations throughout its Gulf and Atlantic coast range, are also present in *P. marinus* populations. The non-coding DNA domain located between the 5S and SSU rRNA genes on the 32 kb genetic element should provide us with the highest degree of interpopulational variability that is possible to detect. Establishing whether or not *P. marinus* has a similar or greater capacity for water-column dispersal or its presence in alternative hosts or reservoirs will be an important consideration in developing sampling strategies to look for geographic strains or races of *P. marinus*.

Example 7

Development of a 'Dilution Endpoint' for *P. marinus* Quantification

Figure 14:
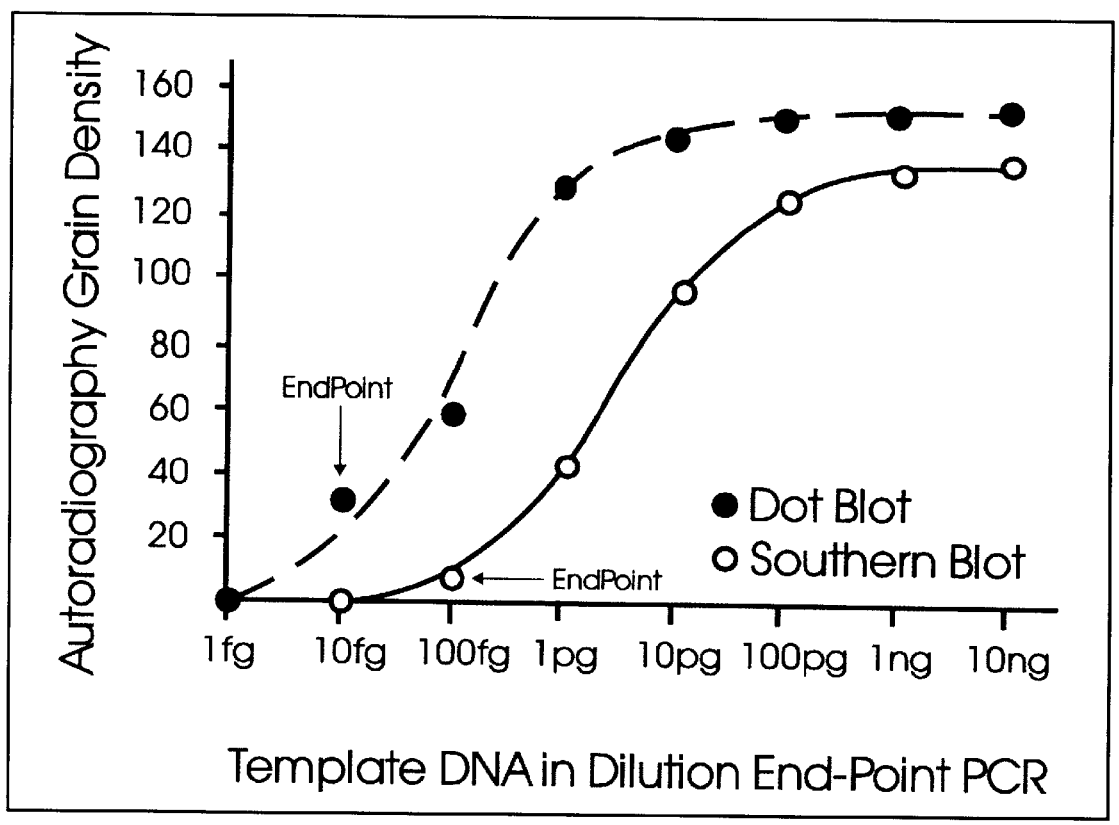
FIG. 14 is a chart showing the standard curves of the dot blot and Southern blot of the amplified *Perkinsus marinus* DNA target as a function of total P. marinus DNA that was used in the amplification.

In order to estimate the amount *P. marinus* DNA from oyster and environmental samples a semi-quantitative methodology was developed based on the PCR that specifically target the NTS region. This method relies on determining the lowest dilution level that is necessary to distinguish any amplification of target by PCR. Because there was no detectable difference either with or without the presence of oyster DNA in the standard-diluted 10-fold with water. A 1 $\mu$l aliquot of each dilution was then used as template in PCR amplifications. Reaction products were dot-blot hybridization signal could no longer be distinguished from the background signal. By assigning a value of '1' to the dilution level at which the amplification signal was extinguished, a titer for *P. marinus* DNA could be estimated for each preceding dilution (FIG. 14). The titer curves for the unknown samples evidence similar sigmoidal saturation kinetics as the standards, demonstrating that the amplification kinetics between the two are identical.

The 'Dilution Endpoint' PCR amplifications thus provide a semi-quantitative estimate ( to the nearest power of 10 in this case) of the initial concentration of *P. marinus* DNA in the oyster hemolymph extracts.

Example 8

Demonstration that Methodology will Detect *P. marinus* DNA in Oyster Samples

Adult commercial oysters (*Crassostrea virgincia*) were collected in 1994 from Tred Avon River in Maryland (n=24) and from Bay Tambour in Louisiana (n=20). A 1.5 ml sample of hemolymph was withdrawn from the adductor muscle through a notch in the shell using a 21-gauge needle. After hemolymph extraction oysters were opened, dissected under microscopy and a 10–20 mg section of mantle tissue from the areas surrounding both labial palpes and rectum was removed. An equivalent section of rectal tissue was also taken. Samples were used for *Perkinsus marinus* screening using the PCR-based assay developed by Marsh et al. (1995) for *P. marinus*.

Figure 15:
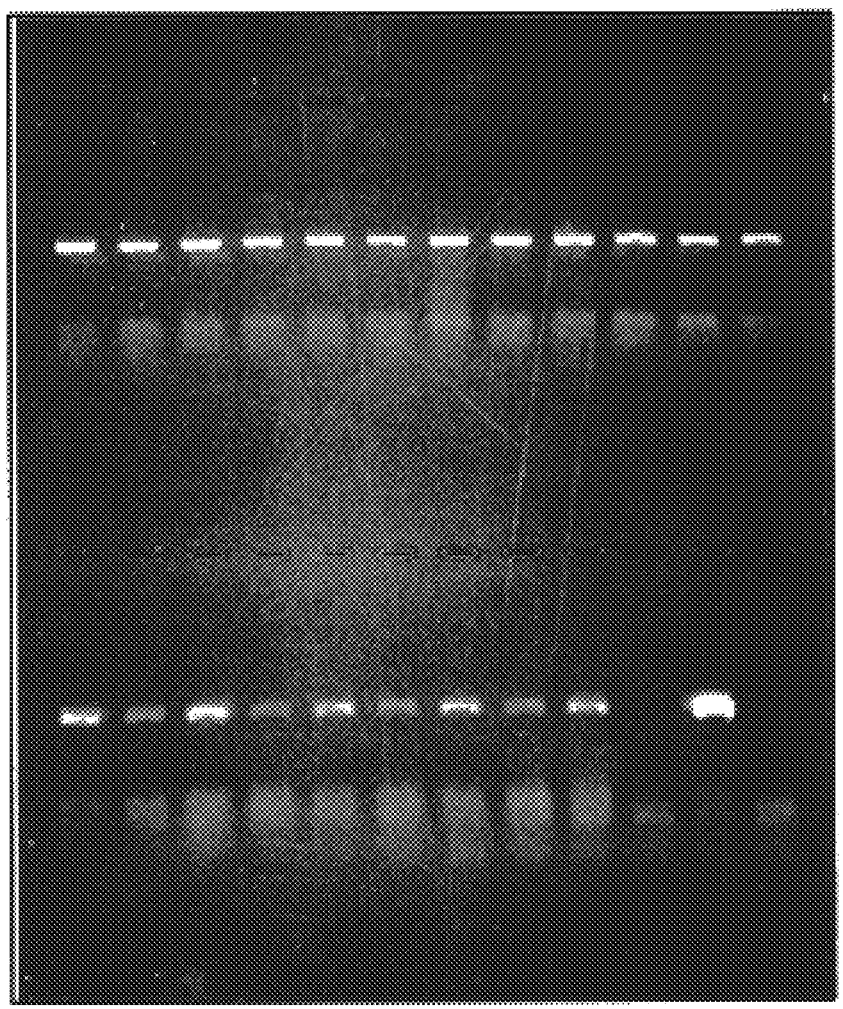
FIG. 15 is an agarose gel electrophoresis of amplified products of PCR demonstrating the presence of *Perkinsus marinus* is samples obtained from the mantle of *Crassostrea virginica* from Louisiana (+): positive control, (−) negative control.

Hemolymph and tissue samples were processed as in Example 2a and 2b respectively. PCR amplification was performed following the protocol described in Example 3b. The PCR was revealed as very accurate and sensible technique for *P. marinus* diagnostic (FIG. 15). Oysters from Maryland, 23 templates (4 from hemocytes, 7 from rectum, 12 from mantle) that were negative by FTM, became positive with PCR for most of the tissues analyzed. There were two templates from hemocytes that were negative by FTM that with PCR became positive.

Example 9

Demonstration that Methodology will Detect *P. marinus* DNA in Clam Samples

Figure 16:
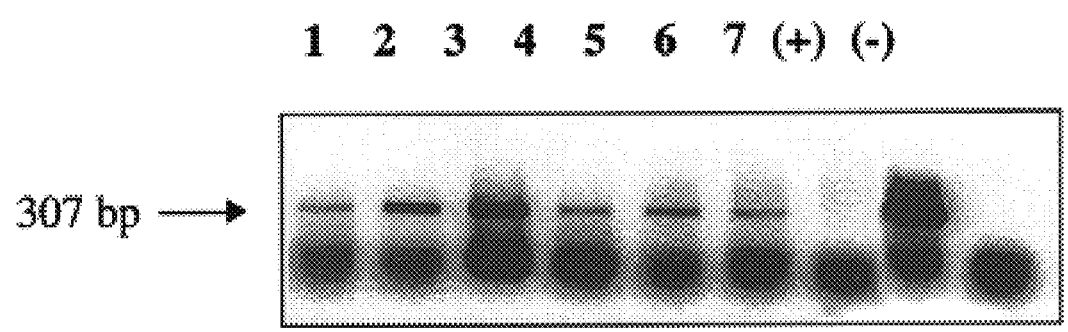
FIG. 16 is an agarose gel electrophoresis of amplified products of PCR demonstrating the presence of *Perkinsus marinus* in samples obtained from *Macoma balthica* from Rhode River. Lanes 1–7: DNA from *M. balthica* individuals, (+): positive control, (−): negative control.

Adult clams (*Macoma balthica* and *Mercenaria mercenaria*) were obtained from the Rhode River in Chesapeake Bay and from the Indian River in Delaware Bay. PCR conditions were as in example 3b. The PCR based assay developed to detect *P. marinus* in oysters, was able to detect the same parasite in clam (*M. balthica*) (FIG. 16).

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rule of law.

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH:1150 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE:NO (v) FRAGMENT TYPE:NA (vi) ORIGINAL SOURCE:Cloned Genomic DNA
        (A) ORGANISM: Perkinsus Marinus
        (B) STRAIN: Texas
        (C) INDIVIDUAL ISOLATE: Texas/1
        (D) DEVELOPMENTAL STAGE: Trophozoites
        (E) HAPLOTYPE: NA
        (F) TISSUE TYPE: NA
        (G) CELL TYPE: Trophozoites
        (H) CELL LINE: TXsc
        (I) ORGANELLE: Plastid-like (viii) POSITION IN GENOME:
        (A) CHROMOSOME/SEGMENT: Extrachromosomal DNA Element
        (B) MAP POSITION: Between 50S and SSU rRNA
        (C) UNITS:

(ix) FEATURE:
        (A) NAME/KEY: SEQ ID NO.1
        (B) LOCATION: NA
        (C) IDENTIFICATION METHOD: By similarity with known sequence
        (D) OTHER INFORMATION: Hypotetical RNA Promoter Sequence (xi) SEQUENCE DESCRIPTION:  SEQ ID NO:1:

```
AAAGTCGCAC CTTTCCCCAT AAACCCCCTC CCCACCCCCT TGGACATTGT TCCACTTTTC      60

ACTTGTATTG TGAAGCACCC AATGCTAGCC CATAGAACAG TCCAGTAGTT CAATAGAGAG     120

ACTAGTGAAC ATAGTTTATA ACATTGTCCA AGGGGTGGAG GGGGATGCGC GAAATCGATG     180

TGCACGTTTG GTCAAAGATG CTCGCGAAAG CTGCACATCA ATTTCGCACA TGGGCGAAAT     240

TGACTTGCAG GTGGGTATAA AAGTTGATGT AGGCCATGTG GCTCGATTTC AACCATATGG     300

GTATGCTTCT GAGGATGGGG TGTTACAGTG GACCATATGA GGTAGGTCAT TTGGAGATGT     360

CACCAAAATG GTCTAAATCT GCGCATTCCA TTTAAGTGAA TTTAAGTGAA ATTTAAGTGA     420

ATTTTACTTA AAATTGACCT TTTTCGTTGC GCAGATTTGG GGTGGTGATG GGTGACGCGG     480

CGAATTTTTT AAAAAAGAGG TATATCGCGT GCTATTTGTA TTTTTGGTAT CACCGCGTCA     540

CCAATCACCA TTGACGGTTT CTTTTTCGAA GTTTTTCCGG ATTATTGCAT TTTTTATATA     600

ATTGTGGGTG GCTGATTCTT GCGAAAGGAC TGTTGTGATG TCCGAGTTCC CAAATTGGGA     660

GTTTTTGGAC ATCACTCCTG ATCTGCCGGC GGCGATCAGG ATGACTGACA TTTCGATATA     720

TTTTGGGTAT TCGATAGCTG CCAAATCGGT CAGCGTCGAG TATTCCGGTT TATTCGAAGG     780

ATTCATGATA TTGCAAAATA TCATTGATTT TCATGGGGTT TTGTATTAGT ACCCGCTCAT     840

TGTGGGAAAG TCGGGTGGAT TTATCTTACC CGCAAATCTA ATACAAGATT TGCATGATGC     900

AGCAATAGAC CAAGGTTAGT ATAGCAGTTG TATTTATACG ACTAGTTATG CAAACCCTTT     960

GTGTTTTTTG TTGCGACTCT TGGCGTGAAC CGGAAGACCG GACCTCGCTT TCGACTATTC    1020

ATCTTTGATG GATATGAGAT CGCAAGGGTA TCGCTTCGTG CGATATTTAG TGACCATCAG    1080

AGCACGCTAC GACTTTTGAT TATATCCTTG GATTTAATCG GAAGCTCGCA AGCATTGCAT    1140

TGATGCAATC                                                           1150
```

(2) INFORMATION FOR SEQ ID NO:2:

(i) SEQUENCE CHARACTERISTICS:
        (A) LENGTH:1545 base pairs
        (B) TYPE: nucleic acid
        (C) STRANDEDNESS: single
        (D) TOPOLOGY: linear (ii) MOLECULE TYPE: DNA(genomic)

(iii) HYPOTHETICAL: NO (iv) ANTI-SENSE: NO (v) FRAGMENT TYPE: NA (vi) ORIGINAL SOURCE: Cloned PCR Product
        (A) ORGANISM: Perkinsus sp.
        (B) STRAIN: MBR
        (C) INDIVIDUAL ISOLATE: MBR/1
        (D) DEVELOPMENTAL STAGE: Trophozoites and Zoospores
        (E) HAPLOTYPE: NA
        (F) TISSUE TYPE: NA
        (G) CELL TYPE: Trophozoites and Zoospores
        (H) CELL LINE: not applicable
        (I) ORGANELLE: Plastid-like (vii) IMMEDIATE SOURCE:
        (A) LIBRARY: not applicable
        (B) CLONE:A8-1500-8, A8-1600-3,A8-1500-2

(viii) POSITION IN GENOME:
        (A) CHROMOSOME/SEGMENT: Extrachromosomal DNA Element
        (B) MAP POSITION: BETWEEN 50S and SSU rRNA
        (C) UNITS: NA (ix) FEATURE:
        (A) NAME/KEY: SEQ ID NO:2:
        (B) LOCATION: NA
        (C) IDENTIFICATION METHOD: By similarity with known sequence
        (D) OTHER INFORMATION: HYPOTETICAL RNA Promoter Sequence (xi) SEQUENCE DESCRIPTION: SEQ ID NO:2:

```
TTTTTGCTTT CACAACCCCG CACCCCATGT ACAATGTTGC CAACCACTAG AGTTTCAACA      60

ACATTCGGAT TTGACAACAT GTCAACAATT CACAACAGAA ATTGCAACA TTGTCACAAA     120

TTCTCAAATT GGACAACATT GGACAAAAAT TCACAACATA CATTGGACAA CAGTGGACAA    180

CGAACCCAAA CCCGACAACA TTGTCCAGGG GGATAGGGGG TGAAAAAGCA GTGCCGGCAA    240

AGTCGAAAGA TGTCAAGTTG GAATGCGGCT CAAATTCGTC ATTTGTGTAA ATCCGCAATT    300

TTGCCAATGT GCAATTTTGC AAATGTGCAA TTTTGCAAAT GTGCAATTTT GCCAATGTGC    360

AATTTTGCAA ATGCGCAATT TTGCAAATCC GCAATTTTGC AAATGTGCAA TTTTGGAAAA    420

TCACCAAATG AAAATCGTCC AAGTCGAATT GGAGGCGTGG TGACATGGTC CCGGGATCCC    480

CTGGTTACAG TGGACAATAT CCCAGCAATA TTCGCTGTAA TTTGGAGTTT CGCTGTTTTG    540

GCAAATTTTG AGTCTGAAAA AAAAAATTGC AAATGCGCAA AGGGGGTGAA GGAAAAAAAA    600

GCACCCCGA AGGTAAAATT CCCTTTAAGT CCCTTGCGCA TTTGCAAAAT TTTCAAAAAT     660

TGTTGCAAAT GCGCTTTTGT TATTTGGCCG GTTCATTGGT GTCAAAAGTT GCCTGGGGTG    720

GTTACACAAT GCACGGAATT GGTTGGAAGT TGTGTGATTG AAAATTGGTC GTGTCACACA    780

ATTTTGCGCA TTTGCAAAAA TTCGCAAATT GGACAAAAAA GGGTCGCGCA CAGTCAAATT    840

GCGCAAATTT CACTTTGAAG TGAGTGCGCA TTTGTGGGGC AGAAATGTGG TGACAGCATC    900

GTTTTTTATA ATAAATATTC TATATTTAGT ATCTTTATTA TAATTTGCTG TCACCAATCA    960

CCATTTTAGA ATTTTTATTT TTTATGTTT TAGTGACCGC GGGATTTTTT GCAAAGTACT    1020

ATTGTGATGT TTGAGTTGTT TGAAATGGGC AATTTAGAAC ATCATCAGAA ATCGCTGAAT   1080

AGTGATTTTT GAGTTTGACT GTTTGAAGTG TTTTGGGTAT TCGGCAGCTG CCAAATCGGT   1140

CAGCGTCGAA TATAATAGCA TTTTTGTGTG TATATGATAT TTAGCGATAT CATTGGAATC   1200

ATGGGGTTTT GTATTAGTAC CCGCTCATTG TGGGAATGTC GGGTGGTTCA ATATCACCTG   1260

CAAATTTAAT ACAGGATTTG CATGATGCAG CGACTGACCG GGGTTGGTAT AATAGCTGAT   1320

TATTCGGCTT ATTATGCAGA CCTATCGTGT TAGTAGTTGC GACTCTTGGC GTGAACCGGA   1380

AGACCGGAAC TTGAATTCGA CTATTTACGT CCGTAAACAG GAGATTTCAA GAATATTGCA   1440
```

```
CATTTTGCGT GATATAAACG TGATCATCTG AGCACGCTTC GACTCTTGGA TATCTGCTAA      1500

TCAGCCGTCA TCTGAGAGCT CGCAAGCATT GCAATTGATG CAATC                     1545
```

(2) INFORMATION FOR SEQ ID NO:3:

(i) SEQUENCE CHARACTERISTICS:
        (A) LENGTH:1413 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: NA (vi) ORIGINAL SOURCE:
        (A) ORGANISM:Perkinsus sp.
        (B) STRAIN:MMIR
        (C) INDIVIDUAL ISOLATE: MMIR/1
        (D) DEVELOPMENTAL STAGE:
        (F) TISSUE TYPE: NA
        (G) CELL TYPE: Trophozoite and Zoospores
        (H) CELL LINE: NA
        (I) ORGANELLE: Plastid-like (vii) IMMEDIATE SOURCE:
        (A) LIBRARY: NA
        (B) CLONE: M5-1500-4, M5-1500-6

(viii) POSITION IN GENOME:
        (A) CHROMOSOME/SEGMENT: Extrachromosomal DNA Element
        (B) MAP POSITION: Between 50S And SSU rRNA (ix) FEATURE:
        (A) NAME/KEY: SEQ ID NO.3
        (B) LOCATION:NA
        (C) IDENTIFICATION METHOD: By Similarity with Known Sequence
        (D) OTHER INFORMATION: Hypotetical RNA Promoter Sequence (x) PUBLICATION INFORMATION: NA (xi) SEQUENCE DESCRIPTION: SEQ ID NO:3:

```
CGTGCCCTTT TCACGAATTC ACAGCCCCGC ACCCCATGTA CAATGTTGCC CACCCGAAAT       60

GCCTGCCTGC CCACCCGAAA TGCCCGAAAT GCCCGTTAGA AAAAGTATGC GAAAAGTTCT      120

TGTCAATTTT GACAGTGTGT GAAAAAACTG AAAAAGTCCA CTCAACATTG CATTATGCAA      180

TTTGCCACTC AACATTGTCC AGGGGGATAG GGGGTGAAAA AGTATCGCAG TCCAACTGAA      240

AAGATGCTAA GTTGAAATGC GGCGCAAATT CATCACTTGA GTTGCGAAAA TCCCTAAAGT      300

CGAATTTGGC ACTCGGTGAC ATGATCGGGA ATTTCCCTGG TTACAGTGGT CAAATCCCAG      360

CAATTTTGGC AAAGTTTTTG AGTTTCGCAC TTTTCGCAAA TTTCGTGTCT GAAAAAAAAA      420

TTTCAACTTT GCGCAAAGGG GTCAAAGGGA AAAAAGCAC CCTCAAAAGG AAATTTCCCT       480

TTAATCCCCT TGAAAAAAA TGCGCAAAGT TAAATTTGCG AAAATTTCGA TTTTCTCATA       540

TGACCGATTA GTTGGTGCCA GATGGTAGTC GGGATGGTTA CACGGTGCAC GGAACTCGTT      600

GGAAGTTCTG GAGTTACGAA TTGGTCCCGT CACCACAATT TGCGCATTTT TGAAATTGCG      660

CAAATTTGCG AAAAAGCAG CGCGCAAAGT TAAATTGTGC GAAAATTGAC TTTCAGGTCG       720

GTGCGCAAAT TTGGGGTGAA AAAGTGGTGA CAGCATCAGA ATTATAATAA ATAATCTATA     780

ATCTAGTTCT TTTATTATAA TTAGCTGTCA CCAATCACCA TTTGAGATTT TTTATTTTTT     840

TATGTTTTAG TGACCGCGGT ATTTTTTCCA GAGTACTATC GTGATGTCTG AGTTGTCTAA     900
```

-continued

```
AACGGCAATT TCAGAACATT ACCAGAAAAC ACTGAATAGT GGTTTCTGAG TCTGACTGTT    960

TGAAGTGTTT TGGGTATTCG GCAGCTGCCA ATTCGGTCAG GGTTGAATAT ACTAACATTT   1020

CTGTGTGTAT ATGGTATTTA GCGATATCAT TGGAATCATG GGGTTTTGTA TTAGTACCCG   1080

CTCATTGTGG GAAAGTCGGG TGGTTCAATA TCACCTGCAA ATTTAATACA GGATTTGCAT   1140

GATGCAGCGA CTGACCGGGG TTAGTATAAT AGCTGATTAT TCGGCTTATT ATGCAGACCT   1200

ATCGTGTTAG TAGTTGCGAC TCTTGGCGTG AACCGGAAGA CCGGAACTTG ATTTCGACTA   1260

TTTACGTCCG TAACACGTCC GTAAACAGGA GATTTCAAGA ATATTGCACA TTTTGTGTGA   1320

TATAATCGTG ATCATCTGAG CACGCTTCGA CTCTTGAATA TTTGTTAAAC AACCGATATT   1380

CGGGAGCTCG CAAGCATTGC AATTGATGCA ATC                                1413
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: NA (vi) ORIGINAL SOURCE: Cloned PCR Product
        (A) ORGANISM: Perkinsus Marinus
        (B) STRAIN: Texas
        (C) INDIVIDUAL ISOLATE: NA
        (D) DEVELOPMENTAL STAGE: Trophozoites
        (E) HAPLOTYPE: NA
        (F) TISSUE TYPE: NA
        (G) CELL TYPE: Trophozoites
        (H) CELL LINE: NA
        (I) ORGANELLE: Plastid-like (vii) IMMEDIATE SOURCE:
        (A) LIBRARY: NA
        (B) CLONE: NA (viii) POSITION IN GENOME:
        (A) CHROMOSOME/SEGMENT: Extrachromosomal DNA Element
        (B) MAP POSITION: NTS Region rRNA Locus
        (C) UNITS: Position 59 to 80 of NTS Region (ix) FEATURE:
        (A) NAME/KEY: primer
        (B) LOCATION: NA
        (C) IDENTIFICATION METHOD: Computer Program (x) PUBLICATION INFORMATION:

(xi) SEQUENCE DESCRIPTION: SEQ ID NO:4:

```
CACTTGTATT GTGAAGCACC C                                               21
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
    (iv) ANTI-SENSE: NO (v) FRAGMENT TYPE: NA (vi) ORIGINAL SOURCE: Cloned PCR Product
         (A) ORGANISM: Perkinsus Marinus
         (B) STRAIN: Texas
         (C) INDIVIDUAL ISOLATE: NA
         (D) DEVELOPMENTAL STAGE: Trophozaites
         (E) HAPLOTYPE: NA
         (F) TISSUE TYPE: NA
         (G) CELL TYPE: Trophozoites
         (H) CELL LINE: TXsc
         (I) ORGANELLE: Plastid-like (vii) IMMEDIATE SOURCE:
         (A) LIBRARY: NA
         (B) CLONE: NA (viii) POSITION IN GENOME:
         (A) CHROMOSOME/SEGMENT: Extrachromosomal DNA Element
         (B) MAP POSITION: NTS Region rRNA Locus
         (C) UNITS: Position 346 to 366 of NTS Region (ix) FEATURE:
         (A) NAME/KEY: primer
         (B) LOCATION: NA
         (C) IDENTIFICATION METHOD: Computer Program
         (D) OTHER INFORMATION: NA (x) PUBLICATION INFORMATION: NA (xi) SEQUENCE DESCRIPTION:  SEQ ID NO:5:

TTGGTGACAT CTCCAAATGA C                                              21

(2) INFORMATION FOR SEQ ID NO:6:

(i) SEQUENCE CHARACTERISTICS:
         (A) LENGTH:20 base pairs
         (B) TYPE:nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (v) FRAGMENT TYPE: NA (vi) ORIGINAL SOURCE: Cloned PCR product
         (A) ORGANISM: Perkimsus Marinus
         (B) STRAIN: Texas
         (C) INDIVIDUAL ISOLATE:
         (D) DEVELOPMENTAL STAGE: Trophozoites
         (E) HAPLOTYPE: NA
         (F) TISSUE TYPE: NA
         (G) CELL TYPE: Trophozoites
         (H) CELL LINE:
         (I) ORGANELLE: Plastid-like (vii) IMMEDIATE SOURCE:
         (A) LIBRARY: NA
         (B) CLONE: MD Mb4, MD Mb5, LA Ma 7

(viii) POSITION IN GENOME:
         (A) CHROMOSOME/SEGMENT: Extrachromosomal DNA element
         (B) MAP POSITION: NTS Region rRNA Locus
         (C) UNITS: Position 82 to 101 of NTS Region (ix) FEATURE:
         (A) NAME/KEY: primer
         (B) LOCATION: NA
         (C) IDENTIFICATION METHOD: Computer program
         (D) OTHER INFORMATION: NA
```

(x) PUBLICATION INFORMATION: NA (xi) SEQUENCE DESCRIPTION: SEQ ID NO:6:

ATGCTAGCCC ATAGAACAGT                                                     20

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (v) FRAGMENT TYPE: NA (vi) ORIGINAL SOURCE: Cloned PCR Product
         (A) ORGANISM: Perkinsus Marinus
         (B) STRAIN: Maryland
         (C) INDIVIDUAL ISOLATE:
         (D) DEVELOPMENTAL STAGE: TROPHOZOITES and Zoospores
         (E) HAPLOTYPE:
         (F) TISSUE TYPE: NA
         (G) CELL TYPE: Trophozoites and Zoospores
         (H) CELL LINE: NA
         (I) ORGANELLE: Plastid-like (vii) IMMEDIATE SOURCE:
         (A) LIBRARY: NA
         (B) CLONE: MD Mb4, MD Mb5, LA MA7

(viii) POSITION IN GENOME:
         (A) CHROMOSOME/SEGMENT: Extrachromosomal DNA Element
         (B) MAP POSITION: MTS Region rRNA Locus
         (C) UNITS: Position 82 to 101 of NTS region (ix) FEATURE:
         (A) NAME/KEY: primer
         (B) LOCATION: NA
         (C) IDENTIFICATION METHOD: Computer Program
         (D) OTHER INFORMATION: NA (x) PUBLICATION INFORMATION: NA (xi) SEQUENCE DESCRIPTION: SEQ ID NO:7:

ATGCTAGCCC ACATCACAGC                                                     20

(2) INFORMATION FOR SEQ ID NO:8:

(i) SEQUENCE CHARACTERISTICS:
         (A) LENGTH:24 base pairs
         (B) TYPE: nucleic acid
         (C) STRANDEDNESS: single
         (D) TOPOLOGY: linear (ii) MOLECULE TYPE: DNA(genomic)

(iii) HYPOTHETICAL: NO (iv) ANTI-SENSE: NO (v) FRAGMENT TYPE: NA (vi) ORIGINAL SOURCE: Cloned PCR Product
         (A) ORGANISM: Perkinsus Marinus
         (B) STRAIN: MBR
         (C) INDIVIDUAL ISOLATE:
         (D) DEVELOPMENTAL STAGE: Trophozoites and Zoospores
         (E) HAPLOTYPE: NA
         (F) TISSUE TYPE: NA

```
            (G) CELL TYPE: Trophozoites and Zoospores
            (H) CELL LINE: NA
            (I) ORGANELLE: Plastid-like (vii) IMMEDIATE SOURCE:
            (A) LIBRARY: NA
            (B) CLONE: A8-1500-8, A8-1500-2, A8-1600-3

(viii) POSITION IN GENOME:
            (A) CHROMOSOME/SEGMENT: Extrachromosomal DNA Element
            (B) MAP POSITION: NTS Region rRNA Locus
            (C) UNITS: Position 441 to 464 of NTS region (ix) FEATURE:
            (A) NAME/KEY:primer
            (B) LOCATION: NA
            (C) IDENTIFICATION METHOD: Computer program
            (D) OTHER INFORMATION: NA (x) PUBLICATION INFORMATION: NA (xi) SEQUENCE DESCRIPTION:  SEQ ID NO:8:

AAGTCGAATT GGAGGCGTGG TGAC                                               24

(2) INFORMATION FOR SEQ ID NO:9:

(i) SEQUENCE CHARACTERISTICS:
            (A) LENGTH:20 base pairs
            (B) TYPE: nucleic acid
            (C) STRANDEDNESS: single
            (D) TOPOLOGY: linear (ii) MOLECULE TYPE: DNA(genomic)

(iii) HYPOTHETICAL: NO (iv) ANTI-SENSE: NO (xi) SEQUENCE DESCRIPTION:  SEQ ID NO:9:

ATTGTGTAAC CACCCCAGGC                                                    20

(2) INFORMATION FOR SEQ ID NO:10:

(i) SEQUENCE CHARACTERISTICS:
            (A) LENGTH:20 base pairs
            (B) TYPE: nucleic acid
            (C) STRANDEDNESS: single
            (D) TOPOLOGY: linear (ii) MOLECULE TYPE: DNA(genomic)

(iii) HYPOTHETICAL: NO (iv) ANTI-SENSE: NO (xi) SEQUENCE DESCRIPTION:  SEQ ID NO:10:

ATGCTAGCCC ATAGAACAGT                                                    20

(2) INFORMATION FOR SEQ ID NO:11:

(i) SEQUENCE CHARACTERISTICS:
            (A) LENGTH:20 base pairs
            (B) TYPE: nucleic acid
            (C) STRANDEDNESS: single
            (D) TOPOLOGY: linear (ii) MOLECULE TYPE: DNA(genomic)

(iii) HYPOTHETICAL: NO (iv) ANTI-SENSE: NO (xi) SEQUENCE DESCRIPTION: SEQ ID NO:11:
```

CATCTCCAAA TGACCTACCT                                        20

(2) INFORMATION FOR SEQ ID NO:12:

(i) SEQUENCE CHARACTERISTICS:
        (A) LENGTH:20 base pairs
        (B) TYPE: nucleic acid
        (C) STRANDEDNESS: single
        (D) TOPOLOGY: linear (ii) MOLECULE TYPE: DNA(genomic)

(iii) HYPOTHETICAL: NO (iv) ANTI-SENSE: NO (xi) SEQUENCE DESCRIPTION: SEQ ID NO:12:

ATGCTAGCCC ACATCACAGC                                        20

(2) INFORMATION FOR SEQ ID NO:13:

(i) SEQUENCE CHARACTERISTICS:
        (A) LENGTH:20 base pairs
        (B) TYPE: nucleic acid
        (C) STRANDEDNESS: single
        (D) TOPOLOGY: linear (ii) MOLECULE TYPE: DNA(genomic)

(iii) HYPOTHETICAL: NO (iv) ANTI-SENSE: NO (xi) SEQUENCE DESCRIPTION: SEQ ID NO:13:

CATCTCCAAA TGACCTACCA                                        20

(2) INFORMATION FOR SEQ ID NO:14:

(i) SEQUENCE CHARACTERISTICS:
        (A) LENGTH:307 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: NA (vi) ORIGINAL SOURCE:
        (A) ORGANISM: Perkinsus Marinus
        (B) STRAIN: Texas
        (C) INDIVIDUAL ISOLATE:
        (D) DEVELOPMENTAL STAGE: Trophozoite
        (E) HAPLOTYPE: NA
        (F) TISSUE TYPE: NA
        (G) CELL TYPE: Trophozoite
        (H) CELL LINE: NA
        (I) ORGANELLE: Plastid-like (vii) IMMEDIATE SOURCE:
        (A) LIBRARY: NA
        (B) CLONE: MD Mb4, MD Mb5,LA MA7

(viii) POSITION IN GENOME:
        (A) CHROMOSOME/SEGMENT: Extrachromosal DNA Element
        (B) MAP POSITION: NTS Region rRNA Locus
        (C) UNITS: Position 60 to 366

(ix) FEATURE:

(A) NAME/KEY: SEQ ID NO.14
        (B) LOCATION:
        (C) IDENTIFICATION METHOD: By similarity with known Sequence
        (D) OTHER INFORMATION: NA (x) PUBLICATION INFORMATION:

(xi) SEQUENCE DESCRIPTION:   SEQ ID NO:14:

CACTTGTATT GTGAAGCACC CAATGCTAGC CCATAGAACA GTCCAGTAGT TCAATAGAGA      60

GACTAGTGAA CATAGTTTAT AACATTGTCC AAGGGGTGGA GGGGGATGCG CGAAATCGAT     120

GTGCACGTTT GGTCAAAGAT GCTCGCGAAA GCTGCACATC AATTTCGCAC ATGGGCGAAA     180

TTGACTTGCA GGTGGGTATA AAAGTTGATG TAGGCCATGT GGCTCGATTT CAACCATATG     240

GGTATGCTTC TGAGGATGGG GTGTTACAGT GGACCATATG AGGTAGGTCA TTTGGAGATG     300

TCACCAA                                                              307

(2) INFORMATION FOR SEQ ID NO:15:

(i) SEQUENCE CHARACTERISTICS:
            (A) LENGTH:307 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL:NO (iv) ANTI-SENSE: NO (v) FRAGMENT TYPE: NA (vi) ORIGINAL SOURCE:
            (A) ORGANISM: Perkinsus Marinus
            (B) STRAIN: Maryland
            (C) INDIVIDUAL ISOLATE:
            (D) DEVELOPMENTAL STAGE: Trophozoite
            (E) HAPLOTYPE: NA
            (F) TISSUE TYPE: NA
            (G) CELL TYPE: Trophozoite
            (H) CELL LINE: NA
            (I) ORGANELLE: Plasid-like (vii) IMMEDIATE SOURCE:
            (A) LIBRARY: NA
            (B) CLONE: LA MA1, LA Mb3, LA MA10

(viii) POSITION IN GENOME:
            (A) CHROMOSOME/SEGMENT: Extrachromosomal DNA Element
            (B) MAP POSITION: NTS Region rRNA Locus
            (C) UNITS: Position 60 to 366

(ix) FEATURE:
            (A) NAME/KEY: SEQ ID NO.15
            (B) LOCATION: NA
            (C) IDENTIFICATION METHOD: By similarity with known sequences
            (D) OTHER INFORMATION: Perkinsus Marinys Type II (x) PUBLICATION INFORMATION:

(xi) SEQUENCE DESCRIPTION:  SEQ ID NO:15:

CACTTGTATT GTGAAGCACC CAATGCTAGC CCACATCACA GCCCAGTAGT TCAATAGAGA      60

GACGAGTGAA CATAGTTTAT AACATTGTCC AAGGGGTGGA GGGGGATGCG CGAAATCGAT     120

GTGCACGTTT GGTCAAAGAT GCTCGCGAAA GCTGCACATC AATTTCGCAC ATGGGCGAAA     180

-continued

| | | | | |
|---|---|---|---|---|
| TTGACTTGCA | GGTGGGTATA | AAAGTTGATG | TAGGCCATGT | GGCTCGATTT CAACCATATG | 240 |
| GGTATGCTTC | TGAGGATGGG | GTGTTACAGT | GGACCATATG | TGGTAGGTCA TTTGGAGATG | 300 |
| TCACCAA | | | | | 307 |

What is claimed is:

1. An oligonucleotide which hybridizes to a nontranscribed spacer sequence between rRNA genes of an organism of the genus PERKINSUS being assayed, wherein said organism of the genus PERKINSUS contains a nucleotide base sequence selected from the group consisting of the sequences shown in FIGS. 2, 3, and 4.

2. The oligonucleotide of claim 1 wherein said organism is *Perkinsus marinus*.

3. The oligonucleotide of claim 2 wherein said sequence is the sequence shown in FIG. 2 (SEQ ID NO:1).

4. The oligonucleotide of claim 1, wherein said sequence is selected from the group consisting of the sequences shown in FIGS. 3 and 4 (SEQ ID NO: 2 and SEQ ID NO: 3).

5. The oligonucleotide of claim 2 wherein said oligonucleotide is one of a pair of PCR primers.

6. The oligonucleotide of claim 5 wherein said oligonucleotide is between about 10 to 35 nucleotides in length.

7. The oligonucleotide of claim 5 wherein said oligonucleotide is between about 15 to 24 nucleotides in length.

8. The oligonucleotide of claim 5, wherein said oligonucleotide is one of a pair of PCR primers selected from the group consisting of:

5'-CAC TTG TAT TGT GAA GCA CCC-3' (SEQ ID NO:4)

5'-TTG GTG ACA TCT CCA AAT GAC-3' (SEQ ID NO:5)

5'-ATG CTA GCC CAT AGA ACA GT-3' (SEQ ID NO:6)

5'-ATG CTA GCC CAC ATC ACA GC-3' (SEQ ID NO:7)

5'-AAG TCG AAT TGG AGG CGT GGT GAC-3 (SEQ ID NO:8)

5'-ATT GTG TAA CCA CCC CAG GC-3' (SEQ ID NO:9)

5'-ATG CTA GCC CAT AGA ACA GT-3' (SEQ ID NO:10)

5'-AGG TAG GTC ATT TGG AGA TG-3' (SEQ ID NO:11)

5'-ATG CTA GCC CAC ATC ACA GC-3' (SEQ ID NO:12)

5'-TGG TAG GTC ATT TGG AGA TG-3' (SEQ ID NO:13).

9. The oligonucleotide of claim 1, wherein said oligonucleotide is detectably labeled.

10. The oligonucleotide of claim 1, wherein said nucleic acid sequence is exactly complementary to said nontranscribed sequence.

11. A method of making an oligonucleotide for use in assaying a target organism of the genus PERKINSUS comprising the steps of:
(i) extracting DNA from said target organism;
(ii) isolating from said DNA a nontranscribed spacer sequence flanked by rRNA genes;
(iii) sequencing said nontranscribed spacer sequence; and
(iv) synthesizing an oligonucleotide having nucleic acid sequence SEQ ID NO:1.

12. The method of claim 11 wherein said nontranscribed spacer sequence is isolated by amplifying said said nontranscribed spacer sequence using primers that preferentially hybridize to said flanking rRNA genes.

13. The method of claim 11 wherein said nontranscribed spacer sequence is isolated by the steps of digesting said DNA with a restriction enzyme, creating a library, and identifying said nontranscribed spacer sequence within said library using a probe specific for one of said rRNA genes.

14. The method of claim 11 wherein said oligonucleotide is one of an pair of PCR primers.

15. A kit for determining the identity of species of a microorganism of the genus PERKINSUS, comprising a container having outwardly directed PCR primer pairs to a nontranscribed spacer sequence flanked by rRNA genes, said primer pairs having a nucleic acid sequence selected from the group consisting of SEQ ID NO: 2 and SEQ ID NO: 3.

16. The kit of claim 15, wherein said microorganism is *PERKINSUS MARINUS* having a nucleic acid sequence SEQ ID NO: 1.

17. The kit of claim 15, wherein said PCR primer pairs are selected from a group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13.

\* \* \* \* \*